(12) United States Patent
Snyder

(10) Patent No.: US 12,727,990 B2
(45) Date of Patent: Sep. 8, 2026

(54) TEMPORARY KERATOPROSTHESIS, CORNEAL TRANSPLANT SUTURING JIG, TEMPORARY ENDOPROSTHESIS, AND METHOD OF USING

(71) Applicant: Michael Snyder, Cincinnati, OH (US)

(72) Inventor: Michael Snyder, Cincinnati, OH (US)

( * ) Notice: Subject to any disclaimer, the term of this patent is extended or adjusted under 35 U.S.C. 154(b) by 663 days.

(21) Appl. No.: 18/134,849

(22) Filed: Apr. 14, 2023

(65) Prior Publication Data

US 2024/0341949 A1 Oct. 17, 2024

(51) Int. Cl.

| | |
|---|---|
| ***A61F 2/14*** | (2006.01) |
| ***A61F 9/007*** | (2006.01) |
| *A61F 2/00* | (2006.01) |

(52) U.S. Cl.

CPC .......... *A61F 2/142* (2013.01); *A61F 9/00727* (2013.01); *A61F 2002/0081* (2013.01); *A61F 2220/0008* (2013.01); *A61F 2250/0059* (2013.01)

(58) Field of Classification Search

CPC .................. A61F 2/142; A61F 9/00727; A61F 2002/0081; A61F 2220/0008; A61F 2250/0059; A61B 17/00; A61B 2017/0409; A61B 2017/0414; A61B 17/0482

See application file for complete search history.

(56) References Cited

FOREIGN PATENT DOCUMENTS

| | | | | |
|---|---|---|---|---|
| CN | 110494156 A | * 11/2019 | .......... | A61K 9/0051 |
| KR | 20170102718 A | * 9/2017 | ............ | A61F 2/142 |

OTHER PUBLICATIONS

Cheung et al., “Basket” mattress suture to manage positive vitreous pressure during penetrating keratoplasty, Canadian Ophthalmological Society, vol. 55, No. 6, pp. 509-517 (Dec. 2020).
Park, “An Improved Temporary Keratoprosthesis”, Retina Today, Sep. 2014.
Cobo, “Ocular Cobo Temporary Keratoprosthesis” 2001 Ocular Instruments.
Eckardt, Vitreq, “Crystal Clear Visulation in Vitreoretinal Surgery”, 2016.
Landers, “Ocular Landers Wide Field Corneal Window” 2001.

* cited by examiner

*Primary Examiner* — Yashita Sharma
*Assistant Examiner* — Hanna L Pasqualini
(74) *Attorney, Agent, or Firm* — The Dobrusin Law Firm, P.C.

(57) ABSTRACT

A temporary keratoprosthesis, a corneal transplant suturing jig, a temporary endoprosthesis, methods of using the same, and kits comprising the same. The temporary keratoprosthesis and corneal transplant comprise grooves into which sutures are located during ophthalmological surgery such that the sutures are prevented from migrating and/or obscuring a view into the eye during surgery. The temporary keratoprosthesis, corneal transplant suturing jig, and temporary endoprosthesis are employed alone or in unison to maintain intraocular pressure during surgery.

20 Claims, 7 Drawing Sheets

D2
A
24
24
20
22
10
24
24
12
AL
D4
14
W
18
D3
24
24
22
20
24
24
A

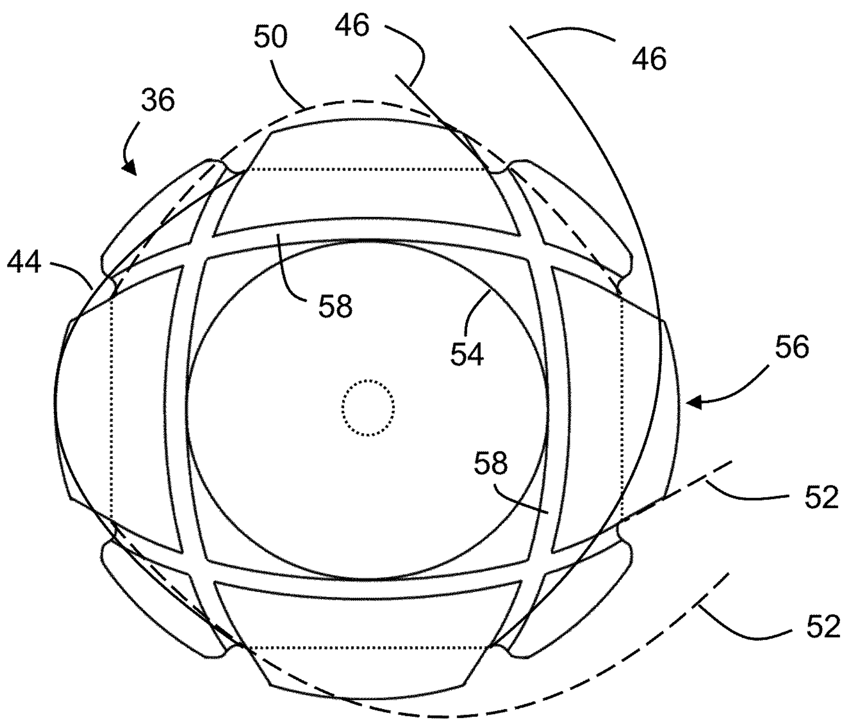
FIG. 2E
FIG. 2F
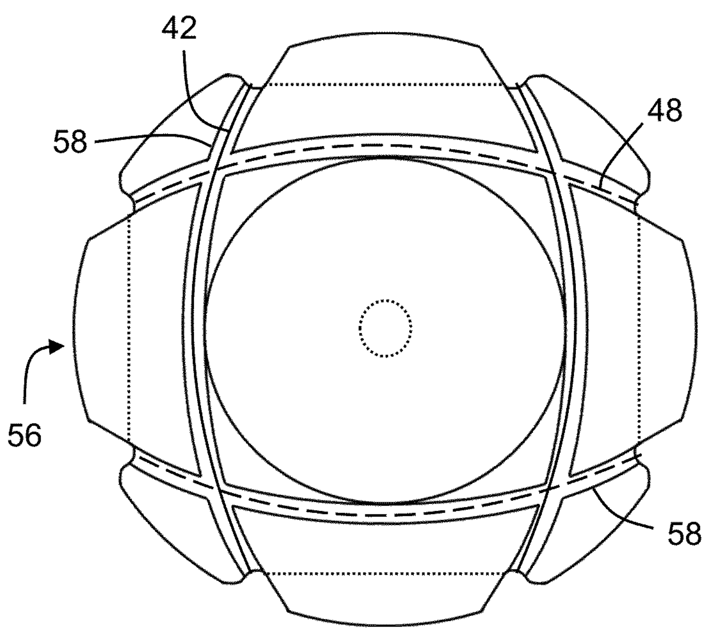

TEMPORARY KERATOPROSTHESIS, CORNEAL TRANSPLANT SUTURING JIG, TEMPORARY ENDOPROSTHESIS, AND METHOD OF USING

FIELD

The present teachings relate to a temporary keratoprosthesis, a corneal transplant suturing jig, a temporary endoprosthesis, methods of using the same, and kits comprising the same. The present teachings may be advantageous for maintaining pressure within an eye during an ophthalmological surgical procedure.

BACKGROUND

Temporary keratoprostheses are conventionally employed for intraoperative implantation when a patient's cornea is too opaque to provide the ophthalmic surgeon with a view into the eye. During an ophthalmological procedure, the cornea is removed, the temporary keratoprosthesis is applied to the eye, a procedure (e.g., repair of a torn and/or detached retina) is performed, the temporary keratoprosthesis is removed, and a transplant cornea (e.g., a transplant cornea from a human donor) is implanted.

The prevalence of patients in need of temporary keratoprosthesis only amounts to approximately 10-40 cases per 1 million people. An alternative technique to a temporary keratoprosthesis employs ocular endoscopy, which is a skill not prevalent even amongst expert retinal surgeons. Moreover, at least some patients in need of a temporary keratoprosthesis are not operated upon due to the risks and hassle upon ophthalmic surgeons who perform the procedure. In other words, the lack of prevalence of relevant cases, the limited ophthalmic surgeon population who performs these procedures, and in some cases an aversion to perform these procedures have hindered development in this field. Moreover, known temporary keratoprostheses have recently been removed from the market due to the aforementioned factors hindering their profitability.

Some temporary keratoprostheses that are employed conventionally are known as the Eckardt keratoprosthesis and the Landers keratoprosthesis. The Eckardt keratoprosthesis is fabricated from silicone and sutures are passed through the silicone to secure the keratoprosthesis to the eye. The Landers keratoprosthesis is fabricated from poly(methyl methacrylate) ("PMMA") and is a dome-shaped prosthesis with six suture holes formed therein. Older technology relative to the Eckardt and Landers devices include the Cobo hand-held keratoprosthesis and the screw-in keratoprosthesis. The Eckardt keratoprosthesis has been in relatively more common use today relative to the Landers keratoprosthesis, though the Eckhardt device is now no longer marketed, as of 2022, and supplies have now dwindled.

Conventional temporary keratoprostheses ("TKP") are subject to a number of challenges, which have contributed to the aversion of ophthalmic surgeons to using the same, as discussed above. The TKPs inadequately seal to the eye and result in leaking of biological fluid of the eye; silicone and other materials from which TKPs are fabricated are prone to fogging with air-fluid exchanges occurring during surgery; the eye with the cornea removed is exposed to the environment for a period of time ("open sky time") prior to and during the TKP being secured to the eye, creating a high risk time window; oil (e.g., silicone oil) employed for specific procedures (e.g., repair of retinal detachment) may be present in the eye, the oil, in one aspect, possibly presenting challenges with marring silicone keratoprostheses and, in another aspect, contributing to a slippery surface for suturing; far peripheral visualization, through the TKP, by the surgeon can be suboptimal; and typically two surgeons must coordinate during the same procedure (e.g., a corneal surgeon to secure the TKP, a retinal surgeon to repair a detached retina, and again the corneal surgeon to remove the TKP and implant a donor cornea), which can inconvenience one or both surgeons and contribute to increased procedure costs. The time-consuming nature of these procedures makes their execution both inefficient and often unprofitable.

Procedures involving full thickness corneal transplant involve cutting a round hole in a patient's cornea, placing a "button" from a donor cornea in the hole, and securing the button with sutures. It is important to ensure that the sutures are evenly distributed in order to avoid post-operative astigmatism. However, it is often difficult to evenly distribute the sutures when the eye is depressurized as a result of the hole cut in the cornea. Typically, until about the first three to five sutures are applied, there is no pressure in the eye and there is a risk of severe bleeding under the retina. Thus, time is of the essence for applying the sutures. Conventionally, specific methods of suturing have been employed to mitigate these challenges. One such example is the mattress suture method described in Cheung et al., "Basket" mattress suture to manage positive vitreous pressure during penetrating keratoplasty, Canadian Ophthalmological Society, Vol. 55. No. 6. pp. 509-17 (December 2020), incorporated herein by reference in its entirety for all purposes. In regard to pressurization, the mattress suture method creates a high posterior pressure in the eye.

Even with brief open sky time (e.g., about 4 minutes or less) following removal of the temporary keratoprosthesis after the retina has been repaired, there is a risk that a retina will again detach due to loss of pressure, necessitating the surgeon to coax the retina back in place. This is due to the need for the surface tension of an air, gas, or oil bubble to keep the retina apposed to the retinal pigment epithelium (RPE) and choroid against the internal eye wall of the eye. If the bubble is not pressurized against the internal eye wall, the retina can again detach. Only after the retina has sealed in place can it remain attached after dissolution of the air bubble or surgical removal of the oil bubble, due to the resumed physiologic action of the RPE creating a suction force.

There is a need for a temporary keratoprosthesis, and a method of using the same, that provides a view to ophthalmic surgeons and protects the eye while an ophthalmological procedure is being performed on a patient in need thereof.

There is a need for a temporary keratoprosthesis, and a method of using the same, that can be secured to an eye in a short time (e.g., about 4 minutes or less, 3.5 minutes or less, or even 3 minutes or less) after the cornea of the eye is incised and/or removed.

There is a need for a temporary keratoprosthesis, and a method of using the same, that can structurally withstand pressures (i.e., without deformation or at least negligible deformation; and without tearing) that build up between the temporary keratoprosthesis and the eye.

There is a need for a temporary keratoprosthesis, and a method of using the same, that can be securely attached to the eye.

There is a need for a temporary keratoprosthesis, and a method of using the same, that is fabricated from fog resistant materials such that the view of ophthalmic surgeons is not impeded.

There is a need for a temporary keratoprosthesis that can maintain full pressurization of the eye for controlled vitreoretinal surgery.

There is a need for a temporary keratoprosthesis, and a method of using the same, that is easy to use and can be attached to the eye with more facile techniques relative to conventional solutions, possibly reducing the time and inconvenience for multiple surgeons cooperating, in tandem, with a procedure.

There is a need for a corneal transplant suturing jig, and a method of using the same, to facilitate the application of sutures, ensure even distribution of sutures, or both.

There is a need for a corneal transplant suturing jig, and a method of using the same, to at least partially pressurize the eye prior to and during the application of sutures during the placement of a full thickness donor corneal transplant.

There is a need for a corneal transplant suturing jig to retain a donor cornea button centrally within the trephination during placement of the sutures (e.g., first, second, or more "cardinal" sutures) securing the donor cornea button in place.

There is a need for a temporary endoprosthesis, and a method of using the same, to maintain pressure in the eye during open sky time, such as after the temporary keratoprosthesis is removed.

The temporary keratoprosthesis, corneal transplant suturing jig, and temporary endoprosthesis of the present teachings, and methods of using the same, address at least some of the needs identified above, including but not limited to providing for a short open sky time (e.g., 3.5 minutes), pressure stability for pressure that builds between the temporary keratoprosthesis and the eye (e.g., able to withstand about 12 mm Hg or more of pressure prior to deformation), secure attachment to the eye (e.g., 8 points of fixation), fog resistance (e.g., by virtue of fabrication from PMMA), and ease of use (e.g., presence of an internal flange for centering and grooves within which pre-placed sutures can be located and then tightened).

SUMMARY

The present teachings provide for a temporary keratoprosthesis for ophthalmological surgery, which may address at least some of the needs identified above. The temporary keratoprosthesis may comprise a body member having a perimeter and a surface into which is defined a first groove and/or a second groove. The first groove may extend generally in a first direction. The second groove may extend generally in a second direction. The first and second grooves may extend between two points arranged adjacent the perimeter of the body member. The first and second grooves may terminate at a notch arranged at each of the two points.

The temporary keratoprosthesis may have a configuration suitable for placement onto an eye and maintaining its general configuration during the ophthalmological surgery.

The first and second grooves may receive pre-placed sutures and prevent the sutures from migrating and/or obscuring a view through the body member.

The first and second grooves may extend partially into a thickness of the body member.

The first and second grooves may have profiles, as viewed on transverse cross-sections of the first and second grooves, that is radiused and/or polygonal.

The first groove may intersect the second groove. The first and second directions may be oriented about 90 degrees to each other.

The surface may be on an anterior side of the temporary keratoprosthesis that is opposing a posterior side thereof, the posterior side being adapted to contact or at least orient toward the eye.

The first and second grooves may extend along an arc of the surface.

The temporary keratoprosthesis may comprise two or more of the first groove and/or two or more of the second groove.

The two or more first grooves and the two or more second grooves may define a boundary around a continuous portion of the surface.

The boundary may be adapted to generally align with and/or circumscribe an incision formed in the eye, as viewed along an axis extending through the temporary keratoprosthesis and an iris of the eye.

The two or more first grooves and the two or more second grooves may form a grid on the surface, as viewed along an axis extending through the first and second sides of the body member. A center section of the grid may generally align with and/or circumscribes an incision formed in the eye, as viewed along an axis extending through the temporary keratoprosthesis and an iris of the eye.

The boundary may be about 5 mm to 10 mm in its largest dimension, preferably about 8 mm.

The boundary may be adapted for light transmission through the anterior and posterior sides of the temporary keratoprosthesis and ultimately through an iris of the eye onto which the temporary keratoprosthesis is placed.

The first and second grooves may be about 0.01 mm to 0.5 mm in their largest dimension as viewed on transverse cross-sections thereof, more preferably about 0.3 mm to 0.4 mm.

A depth of the first and second grooves may be generally equal to or less than a width of the first and second grooves, or vice versa.

Two of the notches of the first and/or second grooves that are in immediate adjacent relationship to each other may be separated by a distance of about 3 mm to 6 mm, preferably about 4.3 mm.

The body member may be about 9 mm to 15 mm in a largest dimension of a profile thereof, preferably about 12 mm.

The body member may be domed.

The anterior side of the temporary keratoprosthesis may have a radius of curvature of about 6.5 mm to 10 mm, preferably about 7 mm.

The posterior side of the temporary keratoprosthesis may have a radius of curvature of about 6.5 mm to 10 mm, preferably about 7 mm.

The posterior side of the temporary keratoprosthesis may comprise a trunk projecting from a first surface of the posterior side and defining a second surface of the posterior side.

A distance between the first and second surfaces may be about 0.2 mm to 1.2 mm, preferably about 0.8 mm.

A minor thickness of the temporary keratoprosthesis may be about 0.1 mm to 3 mm, preferably about 2 mm. A major thickness of the temporary keratoprosthesis may be about 2 mm to 4.5 mm, preferably about 3.19 mm.

The trunk may comprise a radiused surface that terminates at a lip.

The lip may be defined by a minor diameter of about 6 mm to 8.5 mm, preferably about 7.4 mm. The lip may be defined by a major diameter of about 6.5 mm to 9 mm, preferably about 8 mm.

The temporary keratoprosthesis may be fabricated from polymer, glass, or both. The polymer may include silicone, poly(methyl methacrylate), hydrophobic acrylic, hydrophilic acrylic, or any combination thereof. Preferably the temporary keratoprosthesis may be fabricated from poly (methyl methacrylate).

The present teachings provide for a corneal transplant suturing jig for ophthalmological surgery, which may address at least some of the needs identified above. The corneal transplant suturing jig may comprise a body member having a perimeter and a surface into which is defined a first groove and/or a second groove. The first groove may extend generally in a first direction. The second groove may extend generally in a second direction. The first and second grooves may extend between two points arranged adjacent the perimeter of the body member. The first and second grooves may terminate at a notch arranged at each of the two points.

The corneal transplant suturing jig may have a configuration suitable for placement onto an eye and maintaining its general configuration during the ophthalmological surgery.

The first and second grooves may receive pre-placed sutures and prevent the sutures from migrating and/or obscuring a view through the body member.

The first and second grooves may extend partially into a thickness of the body member.

The first and second grooves may have profiles, as viewed on transverse cross-sections of the first and second grooves, that is radiused and/or polygonal.

The first groove may intersect the second groove.

The first and second directions may be oriented about 90 degrees to each other.

The surface may be on an anterior side of the corneal transplant suturing jig that is opposing a posterior side thereof, the posterior side being adapted to contact or at least orient toward the eye.

The first groove and/or the second groove may extend along an arc of the surface.

The body member may comprise a central portion, a first projecting portion, and a second projecting portion.

The central portion may have a circular profile and the first and second projecting portions may project from the central portion.

The first groove may extend along the first projecting portion and the second groove may extend along the second projecting portion.

The first projecting portion may be oriented about 90 degrees to the second projecting portion.

The first and second projecting portions may include two or more first projecting portions and two or more second projecting portions, respectively.

The first and second grooves may include two or more first grooves and two or more second grooves, respectively.

The two or more first grooves and the two or more second grooves may form a grid on the surface.

A center section of the grid may be adapted to locate coaxial with a center of an incision formed in the eye.

The central portion may be defined by a diameter of about 4 mm to 7 mm, preferably about 5 mm.

The two first projecting portions and the two second projecting portions may terminate at a diameter of about 6 mm to 9 mm relative to the center of the body member, more preferably about 7 mm to 8 mm.

The corneal transplant suturing jig may be defined by a radius of curvature of about 6 mm to 9 mm, preferably about 7.5 mm.

The corneal transplant suturing jig may comprise peripheral gaps located between the first and second projecting portions to facilitate placement of one or more sutures for affixing a periphery of a donor cornea to a host cornea.

The corneal transplant suturing jig may be fabricated from polymer, glass, or both. The polymer may include silicone, poly(methyl methacrylate), hydrophilic acrylic, hydrophobic acrylic, or any combination thereof. Preferably the corneal transplant suturing jig may be fabricated from poly(methyl methacrylate).

The present teachings provide for a temporary endoprosthesis for ophthalmological surgery, which may address at least some of the needs identified above. The temporary endoprosthesis may comprise a radially expansile diaphragm and an obturator. The radially expansile diaphragm may comprise a membrane, a cavity defined by the membrane, and a neck.

The obturator, being fed through the neck and into the cavity, may cause the same to radially expand to fill an anterior chamber of an eye.

The cavity may be continuous across a diameter of the membrane or annular.

The membrane may comprise a first segment and optionally a second segment. Where the first segment is present without the second segment, the first segment may extend across the central hole defined by the annular form of the cavity. Where the first segment is present with the second segment, the first and second segments may define the continuous form of the cavity therebetween.

The obturator may be a wire. The wire may be a nitinol wire.

The radially expansile diaphragm may have a diameter, in an expanded state, of about 9 mm to 12 mm.

The radially expansible diaphragm, in a flaccid state, may be about 0.5 mm or more, 1 mm or more, or even 1.5 mm or more in its smallest dimension. The radially expansible diaphragm, in a flaccid state, may be about 3 mm or less, 2.5 mm or less, or even 2 mm or less in its smallest dimension.

The radially expansile diaphragm may be fabricated from silicone, poly(methyl methacrylate), hydrophilic acrylic, hydrophobic acrylic, polytetrafluoroethylene, expanded polytetrafluoroethylene, or any combination thereof.

The present teachings provide for a method for using the temporary keratoprosthesis described above, which may address at least some of the needs identified above. The temporary keratoprosthesis may be applied to an eye of a patient in need of the temporary keratoprosthesis.

The method may comprise making marks at locations where a suture needle is to penetrate the eye. The marks may be made according to the temporary keratoprosthesis (e.g., on or proximate to the notches thereof (e.g., 1 mm or less from the notches)), the corneal transplant suturing jig described above, a physical template, and/or a light guide. The temporary keratoprosthesis, the physical template, and/or the light guide may be applied to the eye prior to making the marks. The temporary keratoprosthesis, the physical template, and/or the light guide may be removed from the eye after making the marks.

The method may comprise pre-placing a first suture and a second suture in the eye according to the marks with the first and second sutures each forming a loop exterior of the eye and free ends of the first and second sutures are left accessible to the exterior of the eye. The loop of the first suture may be oriented 90° to the loop of the second suture.

The method may comprise making an incision in the eye, formed in the cornea, and detaching at least a portion of the cornea from the eye.

The method may comprise applying the temporary keratoprosthesis to the eye.

The method may comprise locating the loops of the first and second sutures within the first and second grooves of the temporary keratoprosthesis, respectively, and pulling the loops of the first and second sutures taught.

The method may comprise securing the free ends of the first and second sutures such that the free ends of the first and second sutures are located within the first and second grooves of the temporary keratoprosthesis, respectively.

The first and second sutures may penetrate a limbus of the eye.

The method may comprise removing the first and second sutures, or un-securing the free ends of the first and second sutures and providing slack to the loops of the first and second sutures.

The method may comprise removing the temporary keratoprosthesis from the eye.

The method may comprise locating a corneal button on the eye.

The method may comprise locating the corneal transplant suturing jig described above onto the eye, over the corneal button.

The method may comprise locating the loops of the first and second sutures within the first and second grooves of the corneal transplant suturing jig, respectively, and pulling the loops of the first and second sutures taught.

The method may comprise securing the free ends of the first and second sutures such that the first and second sutures are located within the first and second grooves of the corneal transplant suturing jig, respectively.

The method may comprise pre-placing a first suture and a second suture in the eye according to the marks with the first and second sutures each forming a loop exterior of the eye and free ends of the first and second sutures are left accessible to the exterior of the eye. The loop of the first suture may be oriented 90° to the loop of the second suture.

The method may comprise locating the loops of the first and second sutures within the first and second grooves of the corneal transplant suturing jig, respectively, and pulling the loops of the first and second sutures taught.

The method may comprise securing the free ends of the first and second sutures such that the first and second sutures are located within the first and second grooves of the corneal transplant suturing jig, respectively.

The method may comprise suturing the corneal button to the eye.

The method may comprise removing the first and second sutures holding the corneal transplant suturing jig to the eye.

The method may comprise removing the corneal transplant suturing jig from the eye.

The method may comprise making an incision (e.g., a peripheral limbal incision) in the eye.

The method may comprise feeding the radially expansile diaphragm described above into an anterior chamber of the eye, while leaving at least a portion of the neck exterior to the eye.

The method may comprise feeding the obturator into the radially expansile diaphragm to expand the radially expansile diaphragm into an iridocorneal angle of the eye.

The radially expansile diaphragm may be fed into the eye prior to making the incision of the eye to remove the portion of the cornea or prior to removing the temporary keratoprosthesis held by the first and second sutures.

The method may comprise removing the obturator from the radially expansile diaphragm.

The method may comprise removing the radially expansile diaphragm from the anterior chamber of the eye through the incision through which the radially expansile diaphragm was fed.

The method may comprise suturing the incision through which the radially expansile diaphragm was fed.

Said removal of the obturator and the radially expansile diaphragm may be performed after suturing the corneal button to the eye.

The method described above relative to the corneal transplant suturing jig may be performed with or without the temporary keratoprosthesis and the steps associated therewith.

The method described above relative to the radially expansile diaphragm may be performed with or without the temporary keratoprosthesis and the steps associated therewith.

The present teachings contemplate that the temporary endoprosthesis, the corneal transplant suturing jig, and the temporary endoprosthesis may be used in a procedure alone or in any combination with each other, with their associated method steps described above.

The present teachings provide for a kit which may address at least some of the needs identified above. The kit may comprise temporary endoprosthesis described above, the corneal transplant suturing jig described above, the temporary endoprosthesis described above, or any combination thereof.

The kit may comprise a first suture, a second suture, a suture needle, a blade (e.g., a trephine blade), a biocompatible ink, one or more medicaments, or any combination thereof.

BRIEF DESCRIPTIONS OF THE DRAWINGS

FIG. 2E illustrates a method according to the present teachings.

FIG. 2F illustrates a method according to the present teachings.

FIG. 5A is a plan view of a temporary endoprosthesis according to the present teachings.

DETAILED DESCRIPTION

Figure 1A:
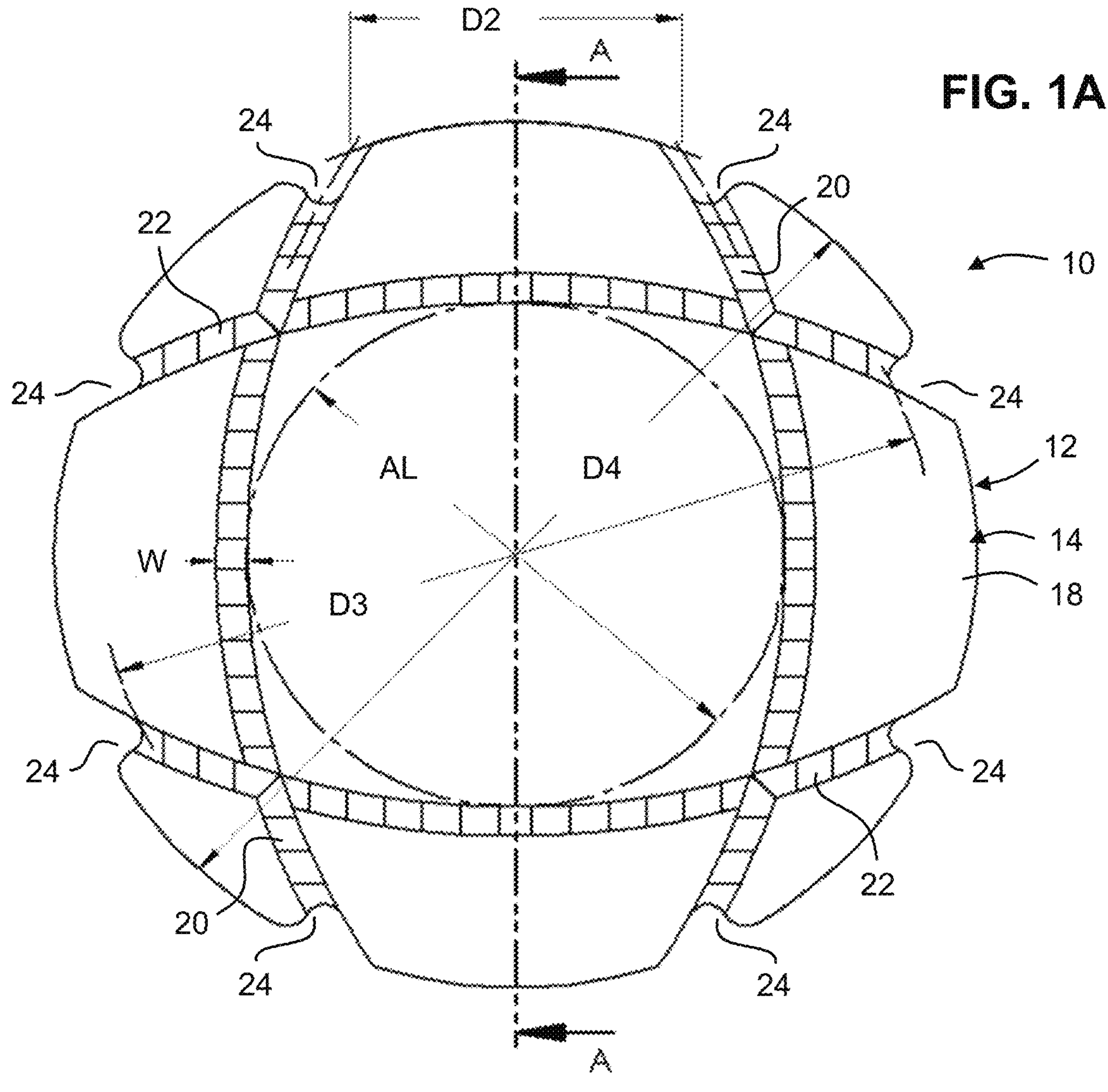
FIG. 1A is an anterior plan view of a temporary keratoprosthesis according to the present teachings.

The temporary keratoprosthesis, the corneal transplant suturing jig, and the temporary endoprosthesis of the present teachings may be used alone or in combination during a procedure. In general, the temporary keratoprosthesis, the corneal transplant suturing jig, and the temporary endoprosthesis of the present teachings may function to maintain intraocular pressure, and substantially mitigate or even prevent damage to the eye. This function may find application with the procedures described herein but is not necessarily limited thereto.

In one aspect, the present teachings may find application in a combined retinal repair procedure and full thickness corneal transplant. In this regard, the patient's cornea may have an opacity that precludes or at least obscures a surgeon's view into the eye, which may be required to perform retinal repair. Thus, a temporary keratoprosthesis may be employed to provide a surgeon with visibility during retinal repair and a corneal transplant suturing jig may be employed to attach a button of a donor cornea or re-attach a button of the patient's cornea that was removed earlier in the procedure. Optionally, a temporary endoprosthesis according to the present teachings may be employed during this procedure.

In another aspect, the present teachings may find application in a full thickness corneal transplant. In this regard, a button of a patient's cornea may be removed, and, in its place, a button of a donor cornea may be located. Optionally, a temporary endoprosthesis according to the present teachings may be employed during this procedure.

The present teachings contemplate several instances in which the eye is depressurized. The eye may be depressurized upon incising the button of the patient's cornea and prior to placement of a temporary keratoprosthesis. The eye may be depressurized upon incising the button of the patient's cornea and prior to placement and at least partially stitching a button of a donor cornea. The eye may be depressurized upon removal of the temporary keratoprosthesis and prior to placement and at least partially stitching a button of a donor cornea.

Regarding placement of the donor cornea (or possibly, in some circumstances, replacement of the patient's cornea), the suturing jig of the present teachings and method of using the same may repressurize the eye while sutures are applied to the cornea button. After applying a suitable quantity of sutures to the cornea button, the eye may remain pressurized, and the suturing jig may be removed.

Prior to, during, and possibly a short time after performing one or both of a full thickness corneal transplant and a retinal repair, a temporary endoprosthesis according to the present teachings may be employed. The temporary endoprosthesis may maintain pressurization in the eye regardless of the location of the patient's cornea button, the donor cornea button, the temporary keratoprosthesis, the suturing jig, or any combination thereof. In this regard, it may be advantageous to use the temporary endoprosthesis in cooperation with the temporary keratoprosthesis, the suturing jig, or both.

The present teachings relate to a temporary keratoprosthesis, a corneal transplant suturing jig, a temporary endoprosthesis, kits thereof, and methods of using the same. The present teachings contemplate that the devices may be used alone or in cooperation with each other during a procedure (e.g., ophthalmological surgery).

By way of example but not limitation, in a procedure involving a retinal repair in an eye with an at least partially translucent or even opaque cornea, a temporary endoprosthesis may be employed to maintain intraocular pressure, a temporary keratoprosthesis may be employed to provide surgeons a view into the eye, and the corneal transplant suturing jig may be employed, after repair of the retina, to hold a donor cornea to the eye during suturing thereof. Optionally, the temporary endoprosthesis and/or the corneal transplant suturing jig may not be employed in the same procedure as the temporary keratoprosthesis.

By way of example but not limitation, in a procedure involving a corneal transplant, a temporary endoprosthesis may be employed to maintain intraocular pressure, and a corneal transplant suturing jig may be employed to hold a donor cornea to the eye during suturing thereof. Optionally, the temporary endoprosthesis may not be employed in the same procedure as the corneal transplant suturing jig.

The devices of the present teachings may find application with reducing the overall procedure time, aiding surgeons in suturing, maintaining intraocular pressure during at least a substantial portion of the procedure (e.g., a total open sky time, during the procedure, of about 3 minutes or less, more preferably 2 minutes or less, more preferably 1 minute or less, or even more preferably 30 seconds or less).

The devices of the present teachings may reduce overall procedure time by reducing the risk of re-damaging the eye (e.g., separation of an already-repaired retina due to loss of intraocular pressure), and/or excessive bleeding, providing a guide for suturing, aiding a surgeon's view to the anterior chamber of the eye via the cornea, or any combination thereof.

The devices of the present teachings may aid surgeons in suturing by providing a guide for suturing, preventing sutures from migrating centripetally, retaining a position of a cornea while secondary sutures are placed, or any combination thereof.

The devices of the present teachings may maintain intraocular pressure by scaling openings into the eye that are formed during the procedure, working cooperatively to maintain a seal of the eye during the same and/or different segments of a procedure (e.g., a retinal repair segment and a corneal transplant segment), being capable of cooperating with the same sutures to hold the devices in-place such that one device may be simply swapped for another, or any combination thereof.

The temporary keratoprosthesis may function to maintain intraocular pressure, provide a view (e.g., a physician's view and/or the view of an imaging device) into the eye, maintain sutures at pre-determined locations, or any combination thereof.

The grooves of the temporary keratoprosthesis, discussed below, may allow sutures to be pre-placed in the eye before the eye is opened (e.g., an incision is made in a cornea). In this regard, the pre-placed sutures may be manipulated into the grooves and tightened to secure the temporary keratoprosthesis to the eye. The grooves may prevent the sutures for migrating centripetally, prevent the sutures from impeding visualization through the temporary keratoprosthesis, or both.

The temporary keratoprosthesis may be employed during ophthalmological surgery. In one sense, the temporary keratoprosthesis may be employed in a retinal repair procedure. In this regard, the temporary keratoprosthesis may be disposed on the eye (e.g., cornea) and/or within a trephination hole formed from removal of at least a portion of a patient's cornea. As a result, the surgeon is provided a clear view, through the temporary keratoprosthesis into the eye so the surgeon can competently manipulate instrumentation to execute a retinal repair.

Typically, the temporary keratoprosthesis is employed in a patient whose cornea is deformed (e.g., opaque) such that a view through the cornea, which is requisite to competently manipulate instrumentation within the eye, is inhibited. Thus, the temporary keratoprosthesis may be applied to the eye after removal of at least a portion of the patient's cornea.

The present teachings contemplate that the temporary keratoprosthesis of the present teachings may be employed in any procedure involving cornea removal (e.g., full thickness cornea removal) where a secondary procedure (e.g., retinal repair) requires instrument manipulation within the eye and a clear view into the eye.

The temporary keratoprosthesis may comprise a body member. The body member may be domed. The body member may have one or more radii of curvature (e.g., convexity) suitable for placement onto the eye (e.g., a cornea of the eye). The body member may have a first side ("anterior side") that orients away from the eye, and a second side ("posterior side") that orients toward the eye. The body member may have a generally circular profile as viewed along a central axis extending through both the first and second sides. The body member may be defined by a perimeter. The first side may have a surface into which one or more grooves are defined.

The anterior side may have a radius of curvature of about 10 mm or less, 9.5 mm or less, or even 9 mm or less. The anterior side of the temporary keratoprosthesis may have a radius of curvature of about 6.5 mm or more, 7 mm or more, 7.5 mm or more, or even 8 mm or more.

The posterior side may have a radius of curvature of about 10 mm or less, 9.5 mm or less, or even 9 mm or less. The posterior side may have a radius of curvature of about 6.5 mm or more, 7 mm or more, 7.5 mm or more, or even 8 mm or more. The radius of curvature of the anterior side may be generally equal to or different from the radius of curvature of the posterior side.

The radii of curvature of the anterior and posterior surfaces may be selected to provide desired magnification properties and/or peripheral view properties for the surgeon and/or imaging devices (e.g., wide field retinal imaging systems).

The average human cornea has a radius of curvature of about 7.6 mm. Typically, operative microscope inverting/visualization systems are designed for the same. However, the radii of curvature of the temporary keratoprosthesis may be modulated to modify the view into the eye.

The anterior side may optionally comprise a trunk. The trunk may function to extend through a trephination hole and aid in maintaining intraocular pressure.

The trunk may be defined by a projection extending from a first surface of the posterior side and may comprise a second surface of the posterior side. The first and second surfaces of the posterior side may be flat, radiused, or both. The trunk may be centrally located on the posterior side. The center of the trunk may be coaxial with the center of the body member.

The trunk may comprise a radiused surface that terminates at a lip. The lip may have a minor diameter of about 8.5 mm or less, 8 mm or less, or even 7.5 mm or less. The lip may have a minor diameter of about 6 mm or more, 6.5 mm or more, or even 7 mm or more. The lip may have a major diameter of about 9 mm or less, 8.5 mm or less, or even 8 mm or less. The lip may have a major diameter of about 6.5 mm or more, 7 mm or more, or even 7.5 mm or more.

The distance between the first and second surfaces may be about 1.2 mm or less, 1 mm or less, or even 0.8 mm or less. The distance between the first and second surfaces may be about 0.2 mm or more, 0.4 mm or more, or even 0.6 mm or more; preferably the distance is about 0.8 mm.

The body member may be about 15 mm or less, 14 mm or less, or even 13 mm or less in a largest dimension of a profile thereof (e.g., diameter). The body member may be about 9 mm or more, 10 mm or more, or even 11 mm or more in a largest dimension of the profile thereof (e.g., diameter).

The body member may have a minor thickness (e.g., defined between the anterior side and the furthest most extent of the second surface defined by the trunk) of about 3 mm or less, 2.5 mm or less, or even 2 mm or less. The body member may have a minor thickness (e.g., defined between the anterior side and the second surface defined by the trunk) of about 0.1 mm or more, 0.5 mm or more, 1 mm or more, or even 1.5 mm or more.

The body member may have a major thickness (e.g., defined between the anterior side and the nearest most extent of the second surface defined by the trunk) of about 4.5 mm or less, 4 mm or less, or even 3.5 mm or less. The body member may have a major thickness (e.g., defined between the anterior side and the nearest most extent of the second surface defined by the trunk) of about 2 mm or more, 2.5 mm or more, or even 3 mm or more.

The body member may be fabricated from a transparent material. The body member may be fabricated from polymer, glass, or both. The polymer may include silicone, PMMA, hydrophobic acrylic, hydrophilic acrylic, or any combination thereof. Preferably the temporary keratoprosthesis may be fabricated from PMMA for its anti-fogging properties and chemical resistance to oil (e.g., silicone oil) and other non-physiological substances that may be employed during ophthalmological surgery.

The temporary keratoprosthesis may withstand intraocular pressure and maintain its general configuration during the ophthalmological surgery. In this regard, one or more dimensions of the temporary keratoprosthesis, discussed herein, may be selected such that deformation of the temporary keratoprosthesis may not be influenced by intraocular pressure (e.g., 10 to 20 mm Hg) or even at higher intraocular pressures.

The temporary keratoprosthesis may comprise one or more grooves. The grooves may function to receive sutures, provide a pre-determined arrangement for sutures, prevent sutures from migrating and/or obscuring a view through the body member, or any combination thereof. The grooves may include two or more first grooves and two or more second grooves. Preferably, the temporary keratoprosthesis comprises two first grooves and two second grooves.

The grooves may be defined into the surface of the first side of the body member. In this regard, sutures can extend over the temporary keratoprosthesis and secure the temporary keratoprosthesis to the eye. The first and second grooves may extend partially into a thickness of the body member.

The first grooves may extend generally in a first direction and the second grooves may extend generally in a second direction. The first direction may be different from the second direction. The first direction may be oriented about 90° or less from the second direction The first direction may be oriented about 30° or more, 50° or more, 70° or more from the second direction. The first grooves may intersect the second grooves.

The first and second grooves may extend along an arc of the body member. That is, the first and second grooves may be defined by radii of curvature. The radius of curvature may be generally equal to or different from the radius of curvature of the first side of the body member. The first and second grooves may be defined by great half circles defined on the radius of curvature of the body member. The two great half circles may form a lune.

The first and second grooves may define a boundary around a continuous portion of the surface of the first side of the body member. The boundary may be adapted to generally align with and/or circumscribe an incision formed in the eye, as viewed along an axis extending through the temporary keratoprosthesis and an iris of the eye.

The first and second grooves may form a grid (e.g., a 3 by 3 grid) on the surface of the first side of the body member, as viewed along an axis extending through the first and second sides of the body member. The center section of the grid may generally align with and/or circumscribes an incision formed in the eye, as viewed along an axis extending through the temporary keratoprosthesis and an iris of the eye.

The boundary may be defined by the intersection of a lune formed by the first grooves and a lune formed by the second grooves may define a viewing window through which a surgeon and/or imaging devices observe the interior of the eye.

The boundary may be adapted for light transmission through the first and second sides of the body member and ultimately through an iris of the eye onto which the temporary keratoprosthesis is placed.

The boundary may be about 10 mm or less, 9 mm or less, or even 8 mm or less in its largest dimension (e.g., arc length). The boundary may be about 5 mm or more, 6 mm or more, or even 7 mm or more in its largest dimension (e.g., arc length).

The first and second grooves may be about 0.5 mm or less, 0.4 mm or less, or even 0.3 mm or less in their largest dimension, as viewed on transverse cross-sections thereof (e.g., a depth measured from the surface and/or a width measured between the surface on opposing sides of the grooves). The first and second grooves may be about 0.01 mm or more, 0.1 mm or more, or even 0.2 mm or more in their largest dimension as viewed on transverse cross-sections thereof (e.g., a depth from the surface and/or a width measured between the surface on opposing sides of the grooves). A depth of the first and second grooves may be generally equal to or less than a width of the first and second grooves, or vice versa.

The first grooves and/or the second grooves may have a profile, as viewed on transverse cross-sections thereof, that is radiused and/or polygonal. That is the corners at the full depth of the first grooves and/or the second grooves may be radiused and/or polygonal. The first groove and/or the second grooves may comprise a chamfer and/or a radius where the first grooves and/or the second grooves meet the surface of the first side of the body member.

The grooves may extend between two points arranged adjacent to (i.e., on or within 2 mm of) the perimeter of the body member. The first and second grooves may terminate at notches arranged at each of the two points. The notches may provide the sutures access to pass across the periphery of the temporary keratoprosthesis.

Two of the notches of the first and/or second grooves that are in immediate adjacent relationship to each other may be separated by a distance of about 3 mm or more, 3.5 mm or more, or even 4 mm or more. Two of the notches of the first and/or second grooves that are in immediate adjacent relationship to each other are separated by a distance of about 6 mm or less, 5.5 mm or less, or even 5 mm or less.

The corneal transplant suturing jig may function to maintain intraocular pressure, hold a cornea button (e.g., a donor cornea button) to an eye for suturing the cornea button to the patient's cornea, maintain sutures at pre-determined locations, or any combination thereof.

The grooves of the corneal transplant suturing jig, discussed below, may allow sutures to be pre-placed in the eye before the eye is opened (e.g., an incision is made in a cornea). In this regard, the pre-placed sutures may be manipulated into the grooves and tightened to secure the corneal transplant suturing jig to the eye. The grooves may prevent the sutures for migrating centripetally.

As referred to herein, cornea button may refer to a generally round portion of a patient's cornea that is removed. Typically, during a full thickness corneal transplant, only a portion of the patient's cornea is removed while another portion of the patient's cornea remains (e.g., at the periphery of the cornea and 1 to 3 mm inward of the periphery). Where reference herein is to a donor button, it is meant that a corneal button is obtained from a donor (e.g., a human donor) and cut with one or more dimensions that are commensurate with one or more dimensions of the patient's cornea which was removed. Typically, the donor button is sutured, around the periphery thereof, to the remainder of the patient's cornea. The donor button may be free or at least substantially free of a deformity (e.g., opacity) that was present in the corneal button that was removed from the patient.

Corneal transplant surgery (e.g., full thickness corneal transplant surgery) may be performed alone or in cooperation with a retinal repair or other secondary procedure discussed herein. During corneal transplant surgery and retinal repairs or other secondary procedures where the eye is depressurized, it may be advantageous to reduce or even substantially eliminate open sky time during which the eye is depressurized. During a corneal transplant, pressurization may not be realized until about 3 or more, 4 or more, or even 5 or more sutures are placed to affix a donor corneal button to the patient's cornea. Pressurization relative to the quantity of stitches may depend on the patient's physiology, the spacing between stitches, and/or other properties of the stitches. In this regard, the corneal transplant suturing jig may hold a donor corneal button to the eye and maintain pressurization of the eye prior to, during, or even after the donor corneal button is stitched to the eye.

As referred to herein, pressurization or maintaining intraocular pressure may mean the normal physiological intraocular pressure (e.g., 10 to 20 mm Hg) or at most 30%, more preferably 20%, or even more preferably 10% less than normal physiological intraocular pressure, understanding that even at partial intraocular pressure, at least some of the detriments to depressurization (e.g., bleeding) may be prevented or at least substantially mitigated.

The corneal transplant suturing jig may comprise a body member. The body member may be domed. The body member may have one or more radii of curvature (e.g., convexity) suitable for placement onto the eye (e.g., a cornea of the eye). The body member may have a first side ("anterior side") that orients away from the eye, and a second side ("posterior side") that orients toward the eye. The body member may be defined by a perimeter. The first side may have a surface into which one or more grooves are defined.

The average human cornea has a radius of curvature of about 7.6 mm. The radii of curvature of the corneal transplant suturing jig may be generally equal to that of the average human cornea. The radius of curvature may be about 6 mm or more, 6.5 mm or more, or even 7 mm or more. The radius of curvature may be about 9 mm or less, 8.5 mm or less, 8 mm or less, or even 7.5 mm or less.

The body member may be about 15 mm or less, 14 mm or less, or even 13 mm or less in a largest dimension of a profile thereof. The body member may be about 9 mm or more, 10 mm or more, or even 11 mm or more in a largest dimension of the profile thereof.

The body member may have a thickness of about 3 mm or less, 2.5 mm or less, or even 2 mm or less. The body member may have a thickness of about 0.1 mm or more, 0.5 mm or more, 1 mm or more, or even 1.5 mm or more.

The body member may comprise a central portion, a first projecting portion, and a second projecting portion. The first and second projecting portions may project from the central portion. The first projecting portions may be oriented about 90° or less from the second projecting portions. The first projecting portions may be oriented about 30° or more, 50° or more, 70° or more from the second projecting portions. The first and second projecting portions may generally form a grid (e.g., a 3 by 3 grid). A center section of the grid may be adapted to located coaxial with a center of an incision formed in the eye.

The body member may comprise two or more first projecting portions and two or more second projecting portions. Preferably the body member comprises two first projecting portions and two second projecting portions.

Peripheral gaps may be disposed between the first and second projecting portions. The peripheral gaps may facilitate placement of one or more sutures for affixing a periphery of a donor cornea to a host cornea. That is, suturing of the donor cornea to the host cornea may involve placing sutures, spanning the donor cornea and host cornea, perimetrically around the donor cornea (e.g., 4 or more, 6 or more, 8 or more, or even 10 or more sutures).

The first grooves may extend along the first projecting portions. The second grooves may extend along the second projecting portions.

The first and second projecting portions may extend to locate adjacent (e.g., at or within 1 mm or less) of a trephination in a host cornea and a diameter of a donor corneal button. The first and second projecting portions may terminate at a diameter of about 9 mm or less, 8.5 mm or less, or even 8 mm or less relative to the center of the body member. The first and second projecting portions may terminate at a diameter of about 6 mm or more, 6.5 mm or more, 7 mm or more, or even 7.5 mm or more relative to the center of the body member.

The central portion may be defined by a diameter of about 7 mm or less, 6.5 mm or less, 6 mm or less, or even 5.5 mm or less. The central portion may be defined by a diameter of about 4 mm or more, 4.5 mm or more, or even 5 mm or more.

The body member may be fabricated from a transparent material. The body member may be fabricated from polymer, glass, or both. The polymer may include silicone, PMMA, hydrophobic acrylic, hydrophilic acrylic, or any combination thereof. Preferably the temporary keratoprosthesis may be fabricated from PMMA for its anti-fogging properties and chemical resistance to oil (e.g., silicone oil) and other non-physiological substances that may be employed during ophthalmological surgery.

The corneal transplant suturing jig may withstand intraocular pressure and maintain its general configuration during the ophthalmological surgery. In this regard, one or more dimensions of the corneal transplant suturing jig, discussed herein, may be selected such that deformation of the corneal transplant suturing jig may not be influenced by intraocular pressure (e.g., 10 to 20 mm Hg) or even at higher intraocular pressures.

The corneal transplant suturing jig may comprise one or more grooves. The grooves may function to receive sutures, provide a pre-determined arrangement for sutures, prevent sutures from migrating, or any combination thereof. The grooves may include two or more first grooves and two or more second grooves. Preferably, the corneal transplant suturing jig comprises two first grooves and two second grooves.

The grooves may be defined into the surface of the first side of the body member. In this regard, sutures can extend over the corneal transplant suturing jig and secure the corneal transplant suturing jig to the eye. The first and second grooves may extend partially into a thickness of the body member.

The first grooves may extend generally in a first direction and the second grooves may extend generally in a second direction. The first direction may be different from the second direction. The first direction may be oriented about 90° or less from the second direction. The first direction may be oriented about 30° or more, 50° or more, 70° or more from the second direction. The first grooves may intersect the second grooves.

The first and second grooves may extend along an arc of the body member. That is, the first and second grooves may be defined by radii of curvature. The radius of curvature may be generally equal to or different from the radius of curvature of the first side of the body member. The first and second grooves may be defined by great half circles defined on the radius of curvature of the body member. The two great half circles may form a lune.

The first and second grooves may be about 0.5 mm or less, 0.4 mm or less, or even 0.3 mm or less in their largest dimension, as viewed on transverse cross-sections thereof (e.g., a depth measured from the surface and/or a width measured between the surface on opposing sides of the grooves). The first and second grooves may be about 0.01 mm or more, 0.1 mm or more, or even 0.2 mm or more in their largest dimension as viewed on transverse cross-sections thereof (e.g., a depth from the surface and/or a width measured between the surface on opposing sides of the grooves). A depth of the first and second grooves may be generally equal to or less than a width of the first and second grooves, or vice versa.

The first grooves and/or the second grooves may have a profile, as viewed on transverse cross-sections thereof, that is radiused and/or polygonal. That is the corners at the full depth of the first grooves and/or the second grooves may be radiused and/or polygonal. The first groove and/or the second grooves may comprise a chamfer and/or a radius where the first grooves and/or the second grooves meet the surface of the first side of the body member.

The grooves may extend between two points arranged adjacent (i.e., on or within 2 mm of) the perimeter of the body member, at termini of the projecting portions. The first and second grooves may terminate at notches arranged at each of the two points. The notches may provide the sutures access to pass across the periphery of the corneal transplant suturing jig.

The temporary endoprosthesis may function to maintain intraocular pressure, provide a view (e.g., a physician's view and/or the view of an imaging device) into the eye, or both.

During retinal repair, corneal transplant surgery, or any other procedure involving depressurization of the eye, even with the temporary keratoprosthesis and/or corneal transplant suturing jig of the present teachings, there may still remain at least short time frames (e.g., 1 minute or less, 30 seconds or less, 20 seconds or less, or even 10 seconds or less) of open sky time. For example, prior to applying a corneal transplant suturing jig to an eye, there is a period of time in which a donor corneal button is not present on the eye and/or the donor corneal button is being manipulated into place on the eye.

In this regard, the temporary endoprosthesis may be employed to prevent or even substantially mitigate the open sky time during these types of events. The temporary endoprosthesis may be introduced into the eye prior to any corneal incision and remain in the eye until the donor corneal button is sutured to the patient's remaining cornea and pressurization is realized.

The temporary endoprosthesis may be located into the anterior chamber of an eye. The temporary endoprosthesis may extend across the largest dimension of the anterior chamber, defined by the iridocorneal angle. In this regard, the temporary endoprosthesis may seal the anterior chamber from the posterior chamber of the eye and maintain pressurization, at least in the posterior chamber.

The temporary endoprosthesis may comprise a radially expansile diaphragm. The radially expansile diaphragm may function to maintain intraocular pressure, act as a fluid barrier between the anterior and posterior chambers of the eye, or both.

The temporary endoprosthesis may be located within and radially expand to fill an anterior chamber of an eye. The temporary endoprosthesis may located into the iridocorneal angle of the anterior chamber.

The radially expansile diaphragm may have a diameter, in an expanded state, of about 9 mm or more, 9.5 mm or more, or even 10 mm or more. The radially expansile diaphragm may have a diameter, in an expanded state, of about 12 mm or less, 11.5 mm or less, or even 11 mm or less.

The radially expansile diaphragm may comprise a membrane. The membrane may function to span across the anterior chamber to form a barrier between the anterior and posterior chambers of the eye.

The membrane may comprise a first segment and optionally a second segment. In one aspect, the cavity may be continuous and thus, may be defined between the first and second segments. The first segment may be oriented toward the cornea of the eye and the second segment may be oriented toward the retina of the eye.

In another aspect, the cavity may be annular and thus the interior or central hole defined by the annular form may be occupied by the membrane radially spanning thereacross.

The radially expansile diaphragm may be fabricated from silicone, PMMA, hydrophilic acrylic, hydrophobic acrylic, polytetrafluoroethylene (PTFE), expanded polytetrafluoroethylene (ePTFE), or any combination thereof.

The radially expansile diaphragm may comprise a cavity. The cavity may function to receive an obturator as discussed below. The cavity may be continuous across the largest dimension (e.g., diameter) thereof. The cavity may be annular.

The radially expansile diaphragm may comprise a neck. The neck may function to receive the obturator and provide access to the cavity. The neck may extend through an incision through which the radially expansile diaphragm is introduced into the eye. At least a portion of the neck may be exposed to the exterior of the eye. Such exposure may be maintained throughout the procedure.

The temporary endoprosthesis may comprise an obturator. The obturator may function to cause the radially expansile diaphragm to expand to fill an anterior chamber of the eye.

The obturator may include a wire. The wire may be fed, through the neck, into the cavity. The obturator may be flexible enough to feed or expand peripherally around the cavity and rigid enough to maintain the radially expansile diaphragm in an expanded state An exemplary obturator may include a nitinol wire confirming to ASTM F2063-18.

The present teachings contemplate the temporary keratoprosthesis, corneal transplant suturing jig, temporary endoprosthesis, or any combination thereof may be included in a kit. The kit may be provided to surgeons such that they are equipped for performing the method described herein.

The kit may further comprise one or more sutures, suture needles, trephine blades, biocompatible inks, medicaments, or any combination thereof.

The present teachings provide for a method for using the temporary keratoprosthesis, corneal transplant suturing jig, and temporary endoprosthesis described herein. The method may be performed on an eye of a patient in need of a temporary keratoprosthesis, corneal transplant suturing jig, temporary endoprosthesis, or any combination thereof.

The method may comprise one or more of the following steps. Some of the steps may be duplicated, removed, rearranged relative to other steps, combined into one or more steps, separated into two or more steps, or a combination thereof.

As discussed throughout the present teachings, the temporary keratoprosthesis, corneal transplant suturing jig, and temporary endoprosthesis may be used individually during a procedure or in combinations with each other. Accordingly, the following method may be understood as illustrative of both the individual and combined uses.

The method may comprise making marks at locations where a suture needle is to penetrate the eye. The marks may be made according to the temporary keratoprosthesis, the corneal transplant suturing jig, a physical template, a light guide, or the like. The same may be applied to the eye, marks may be made, and then the article for guiding the marks may be removed from the eye. The marks may be made with a biocompatible ink.

The method for making marks described above may apply to the corneal suturing jig, whether used with or without the temporary keratoprosthesis in a procedure. The same or different marks as the temporary keratoprosthesis may be employed for the corneal transplant suturing jig.

The method may comprise pre-placing a first suture and a second suture in the eye. The first and second sutures may be placed according to the marks described above. The sutures may be placed such that a loop is formed in each suture and free ends of the first and second sutures are left accessible to the exterior of the eye. Parallel double-stranded or one or more second sets of suture may be employed.

In this regard, the suture needles, with the sutures attached, may penetrate the eye at a first point, extend a length underneath a surface of the eye, penetrate the eye at a second point to expose the suture needles at an exterior of the eye, penetrate the eye at a third point, extend a length underneath the surface of the eye, and penetrate the eye at a forth point to expose the suture needles at an exterior of the eye. The sutures may be cut from the suture needles to define free ends thereof. The opposing free end may be left extending from the first penetration point. The suture needles may penetrate a limbus of the eye, the cornea of the eye, the sclera of the eye, or any combination thereof. Preferably the suture needles penetrate a limbus of the eye.

The penetration points may be located at eight corners of an octagon, where the corners are associated with a first and second pair of opposing sides of the octagon. The loops may be defined between the second and third penetration points.

The loop of the first suture may be oriented at an angle to the loop of the second suture. The angle may be about 30° or more, 40° or more, or even 50° or more. The angle may be about 90° or less, 80° or less, 70° or less, or even 60° or less.

Other suturing arrangements are within the scope of the present teachings depending on the configuration of the grooves formed in the temporary keratoprosthesis and/or corneal transplant suturing jig.

The suturing method described above may apply to the corneal suturing jig, whether used with or without the temporary keratoprosthesis in a procedure. The same or different sutures as the temporary keratoprosthesis may be employed for the corneal transplant suturing jig.

The method may comprise making an incision in the eye. The incision may be formed in the cornea. The incision may detach at least a portion of the cornea from the eye. The incision may form a corneal button.

It is understood that the corneal incision may be made for a procedure involving the temporary keratoprosthesis or any other procedure where a corneal transplant suturing jig may be used (e.g., without the temporary keratoprosthesis).

The method may comprise applying the temporary keratoprosthesis to the eye. The temporary keratoprosthesis may cover the trephination hole left by the incision. The temporary keratoprosthesis may be centered to the trephination hole. Where the temporary keratoprosthesis comprises a trunk, the trunk may be located into the trephination hole.

The method may comprise locating the loops of the first and second sutures within the first and second grooves of the temporary keratoprosthesis, respectively. The method may comprise pulling the loops of the first and second sutures taught. The method may comprise securing the free ends of the first and second sutures such that the free ends of the first and second sutures are located within the first and second grooves of the temporary keratoprosthesis, respectively. The free ends can then be wrapped, tied, knotted, tucked away, cut, or any combination thereof.

After securing the temporary keratoprosthesis to the eye, a secondary procedure such as a retinal repair may be performed. The temporary keratoprosthesis may maintain intraocular pressure and provide a view into the eye during the secondary procedure. After the secondary procedure is completed, the temporary keratoprosthesis may be removed.

The method may comprise removing the first and second sutures or un-securing the free ends of the first and second sutures and providing slack in the loops of the first and second sutures. In one aspect, a corneal transplant suturing jig may be secured to the eye with the same sutures as the temporary keratoprosthesis. In another aspect, new sutures may be located in the eye in accordance with a similar procedure as described above. Typically, the same sutures may be used, however, there may be circumstances in which new sutures may be employed. Where new sutures are employed, the same penetration points as for the temporary keratoprosthesis may be employed or new penetration points may be formed.

The method may comprise removing the temporary keratoprosthesis from the eye, locating a corneal button (e.g., donor corneal button) on the eye, and locating the corneal transplant suturing jig onto the eye, over the corneal button.

Whether used in with or without the temporary keratoprosthesis in a procedure, the loops of the first and second sutures may be located within the first and second grooves of the corneal transplant suturing jig, respectively, and pulled taught. The free ends of the first and second sutures may be secured such that they are located within the first and second grooves of the corneal transplant suturing jig, respectively.

The method may comprise suturing the corneal button to the eye. The sutures may span the corneal button and the patient's remaining cornea. The sutures may be placed perimetrically around the corneal button. The sutures may include 4 or more, 6 or more, 8 or more, or even 10 or more sutures. After about 4 or more sutures are placed, intraocular pressure may be maintained. After all the sutures are placed, the corneal transplant suturing jig may be removed from the eye.

The first and second sutures holding the corneal button may be loosened and/or removed from the eye and the corneal transplant suturing jig may be removed from the eye.

The temporary endoprosthesis according to the present teachings may be employed in cooperation with the temporary keratoprosthesis and/or the corneal transplant suturing jig. The temporary endoprosthesis may be employed to maintain intraocular pressure while the temporary keratoprosthesis and/or the corneal transplant suturing jig are not applied to the eye.

The method may comprise making an incision in the eye. The incision may be a peripheral limbal incision. The incision may be about 4 mm or less, 3 mm or less, 2 mm or less, or even 1 mm or less in its largest dimension.

The method may comprise feeding the radially expansile diaphragm through the incision and into an anterior chamber of the eye. At least a portion of the neck may be left exterior to the eye.

The method may comprise feeding the obturator into the radially expansile diaphragm. The obturator may be fed through the neck and into the cavity of the radially expansile diaphragm. Feeding of the obturator may cause the radially expansile diaphragm to radially expand the same into the iridocorneal angle of the eye.

The temporary endoprosthesis may be introduced into the eye prior to making the incision in the eye to remove the portion of the cornea or prior to removing the temporary keratoprosthesis held by the sutures.

The method may comprise removing the obturator from the radially expansile diaphragm and removing the radially expansile diaphragm from the anterior chamber of the eye. The radially expansile diaphragm may be removed through the incision through which it was fed into the eye. The incision may then be sutured. Removal of the temporary endoprosthesis may be performed after suturing the corneal button (e.g., donor corneal button) to the eye.

It is understood that the method of using the temporary endoprosthesis may be performed in a procedure with or without the temporary keratoprosthesis and/or the corneal transplant suturing jig.

Turning now to the drawings, it is understood that the drawings are meant to be illustrative and not limiting. The drawings may not be to scale, and those skilled in the art should recognize that portions of the articles are not shown in order to help avoid obscuring certain of the features. Any elements or features not shown in the drawings but otherwise described herein may be understood to be employable with the depicted articles. Any method steps depicted and described in a certain order are not meant to solely be limited to that order. The method described herein may be performed in any way that is practicable as understood by those skilled in the art through the present teachings.

Figures 1B, 1C:
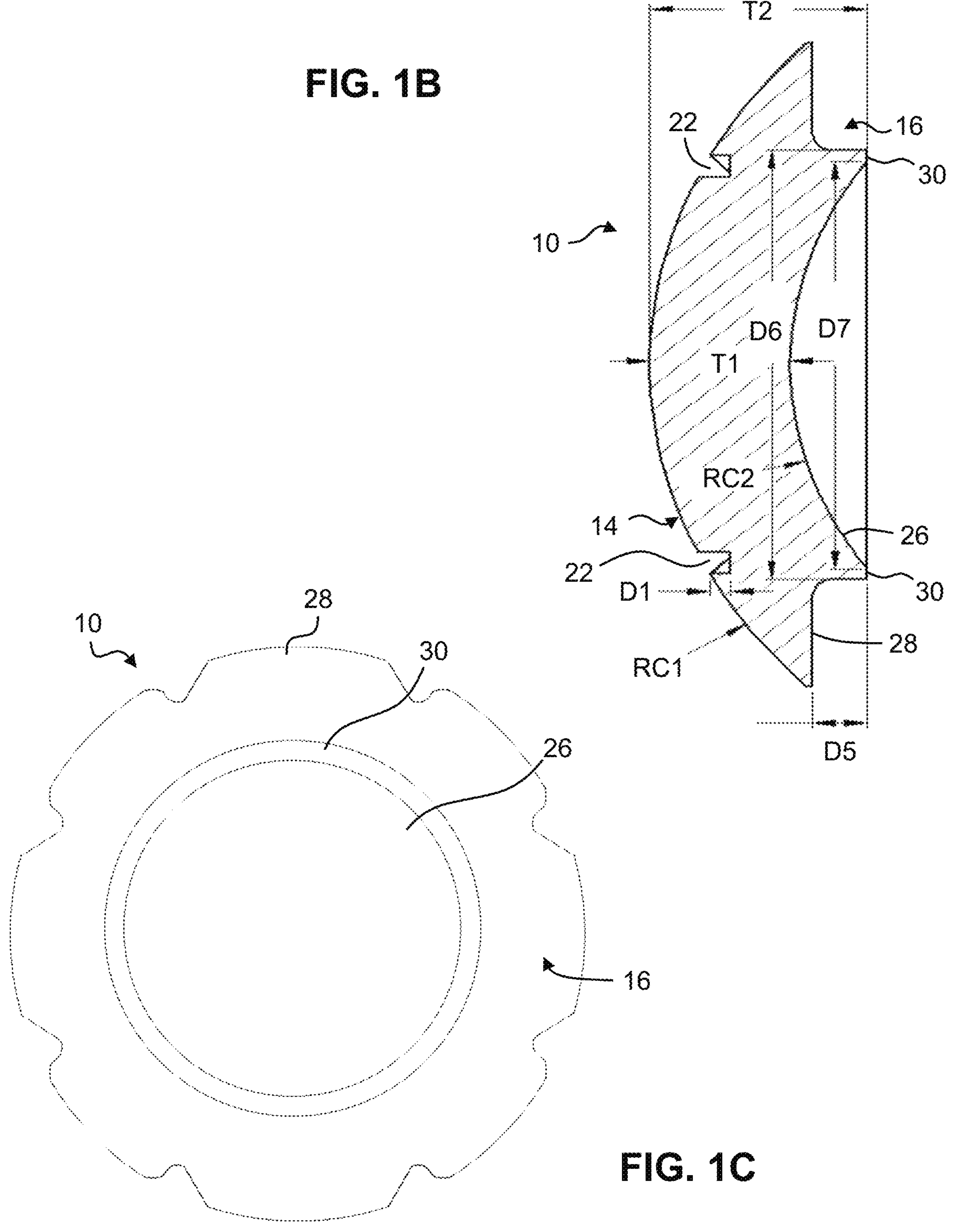
FIG. 1B is a sectional view of the temporary keratoprosthesis viewed along a line A-A.
FIG. 1C is a posterior plan view of the temporary keratoprosthesis.

FIG. 1A through FIG. 1C illustrate a keratoprosthesis 10 according to the present teachings. The keratoprosthesis 10 comprises a body member 12, a first side 14 of which is depicted in FIG. 1A and a second side 16 of which is depicted in FIG. 1C (both of which are depicted in FIG. 1B). The first side 14 may be also referred to herein as the anterior side and the second side 16 may also be referred to herein as the posterior side. The first side 14 has a surface 18 into which two first grooves 20 and two second grooves 22 are formed. The first and second grooves 20, 22 terminate at a perimeter of the body member 12 with notches 24, there being eight notches depicted, referring to FIG. 1A.

The first and second grooves 20, 22 define a boundary around a continuous portion of the surface 18. The boundary is defined by an arc length AL. Reference is made to FIG. 1B, which depicts the curvature of the surface 18.

The first and second grooves 20, 22 are defined by a depth D1, measured from the surface 18, and a width W, measured between opposing sides of the grooves 20, 22. The present teachings contemplate that sutures typically employed in ophthalmology have a diameter of about 0.01 mm to 0.04 mm. Accordingly, the depth D1 and/or width W of the grooves 20, 22 may be commensurate with the diameter of the sutures employed or may be larger than the diameter of the sutures to assist in locating the sutures within the grooves 20, 22.

Two notches 24 of the first grooves 20 that are in immediate adjacent relationship to each other are separated by a distance D2. The same is applicable to the notches 24 of the other grooves 20, 22 that are in immediate adjacent relationship to each other. As illustrated, the distance D2 is measured center-to-center, with respect to a transverse cross-sectional profile of the grooves 20, 22.

Two notches 24 of the second grooves 22 that are located on opposing ends of the body member 12 are separated by a distance D3. The same is applicable to the notches 24 of the other grooves 20, 22 that are diagonally opposed to each other. As illustrated, the distance D3 is measured center-to-center, with respect to a transverse cross-sectional profile of the grooves 20, 22.

A profile of the body member 12 is defined, in its largest dimension, with a diameter D4. The first and second sides 14, 16 of the body member 12, or at least a portion thereof, may be defined by radii of curvature. The radius of curvature RC1 of the first side 14 may be generally equal to or different from the radius of curvature RC2 of the second side 16.

The first side 14 and the second side 16 are separated by a minor thickness T1. The first side 14 and the second side 16 are separated by a major thickness T2.

The second side 16 of the body member 12 includes a radiused surface 26 and a planar surface 28. The radiused surface 26 terminates at a lip 30, which is offset by a distance D5 from the planar surface 28. The lip 30 is defined by a major diameter D6 and a minor diameter D7. The lip 30 defines a trunk according to the present teachings.

The present teachings contemplate that the illustrated keratoprosthesis is meant to be exemplary and not limiting. By way of example, any number, orientation, location, and cross-sectional profile of grooves described herein may be employed in the illustrated keratoprosthesis. The keratoprosthesis illustrated may include one or more other features discussed herein and not depicted and/or the keratoprosthesis of the present teachings may omit one or more depicted features.

FIG. 2A through FIG. 2F illustrate a method of using a keratoprosthesis 56.

Figure 2A:
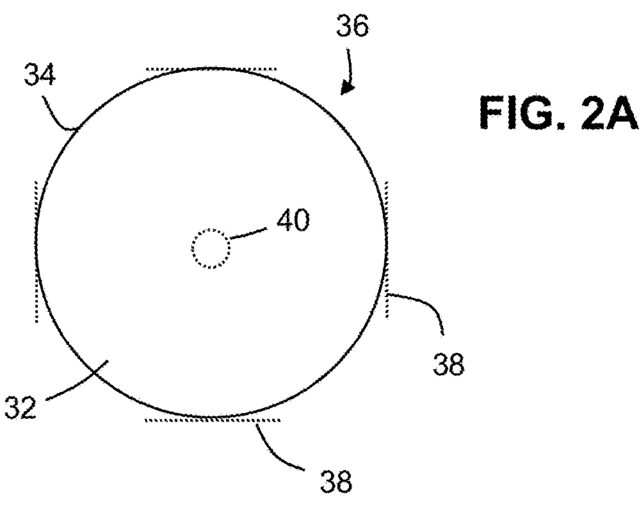
FIG. 2A illustrates a method according to the present teachings.

In FIG. 2A, prior to any incisions or placement of sutures, the cornea 32 and the limbus 34 of an eye 36 may be marked to identify the proper location of both suture placement and corneal trephination. The marks may be generally tangential to the limbus 34 or possibly a concentric boundary about 2 mm or less, 1 mm or less, or even 0.5 mm or less interior to the limbus 34. Four marks 38 are made in the manner of alternating sides of an octagon, such that there are two pairs of opposing parallel marks 38, whereby a first pair is generally orthogonal to a second pair. A fifth mark 40 indicates the centration for trephination for the corneal opening.

The present teachings contemplate that a keratoprosthesis as described herein, a physical template, a light guide, or otherwise may be employed to mark the location on the eye where a suture needle is to penetrate and to identify the center of the eventual trephination as shown in FIG. 2A. In this regard, the keratoprosthesis as described herein, the physical template, the light guide, or otherwise may be temporarily placed on the eye, marks may be made (e.g., with a biocompatible ink), the keratoprosthesis as described herein, the physical template, the light guide, or otherwise may be removed, and the sutures may be applied. The marks may be made proximate to the notches shown in FIG. 1A (e.g., at or within 1 mm or less of the notches), preferably on or within the perimeter of the keratoprosthesis, corresponding with the distance between notches in immediate adjacent relationship to each other.

Figure 2B:
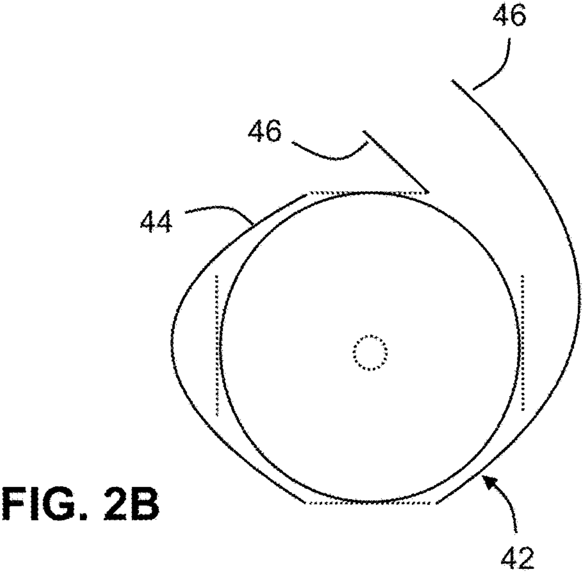
FIG. 2B illustrates a method according to the present teachings.

In FIG. 2B, a first suture 42 is located in and/or near the limbus 34 such that two long partial thickness bites are taken along two of the marks 38, creating a loop 44. Abundant slack is left the loop 44 and two free ends 46 of the first suture 42 are left exposed and untied.

Figure 2C:
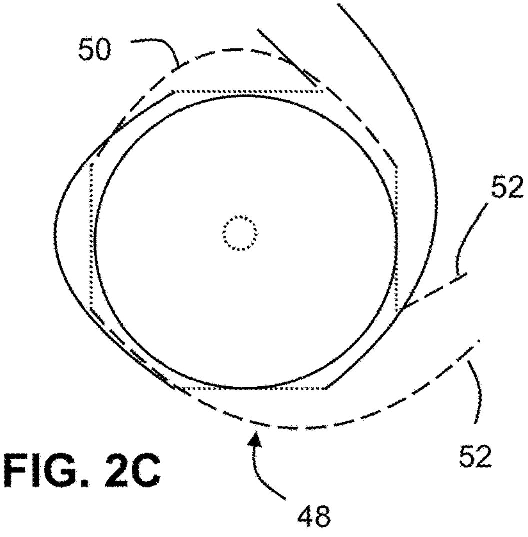
FIG. 2C illustrates a method according to the present teachings.

In FIG. 2C, a second suture 48 is located in and/or near the limbus 34 with two long partial thickness suture bites, placed similarly relative to the first suture 42, along two of the marks 38, creating a loop 50. Abundant slack is left in the loop 50 and two free ends 52 of the second suture 48 are left exposed and untied.

In the areas where the sutures 42, 48 extend along the marks 38, 40, the sutures extends underneath the surface of the eye 36. Abundant slack is left in the loops 44, 50, and the two free ends 46, 52, respectively of the first and second sutures 42, 48 are left exposed, which will be addressed as provided below.

Figure 2D:
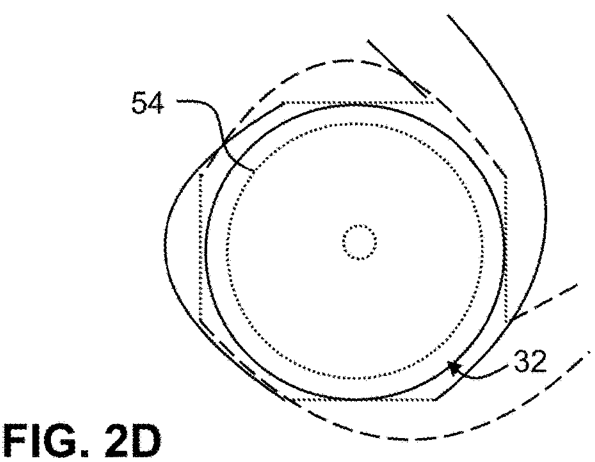
FIG. 2D illustrates a method according to the present teachings.

In FIG. 2D, a corneal trephination is performed to remove a central round button in the patient's cornea 32 and to form a trephination hole 54. The diameter of the trephination hole 54 is generally commensurate with the major diameter D6 of the lip 30 on the posterior side 16 of the temporary keratoprosthesis device 10, shown in FIG. 1B.

In FIG. 2E, a keratoprosthesis 56 is located over the eye 36 and into the trephination hole 54 formed by the removal of the central round button of the patient's cornea, preferably with the grooves 58 circumscribing the trephination hole 54, The keratoprosthesis 56 may then rotated so that the notches 60 correspond in location to each partial thickness pass of the sutures 42, 48.

The loops 44, 50 of the first and second sutures 42, 48 can then be pulled over the keratoprosthesis 56 and located into the grooves 58 thereof. It can be seen that the grooves 58 generally circumscribe the trephination hole 54, as viewed on an axis providing the plan view. With the keratoprosthesis 56 in this position, the surface of the eye 36 is located between the keratoprosthesis 56 and the portions (shown with dotted lines) of the first and second sutures 42, 48 extending underneath the surface. The physician performing the procedure ensures that the loops 44, 50 of the sutures 42, 48 are located completely into the grooves 58 formed in the keratoprosthesis 56 before proceeding to the next step.

The free ends 46, 52 of the first and second sutures 42, 52 are pulled taught to secure the keratoprosthesis 56 to the eye 36. As the free ends 46, 52 are pulled taught, the portions of the first and second sutures 42, 52 leading to the free ends 46, 52 are located into the grooves 58. The free ends 46, 52 can then be wrapped, tied, knotted, tucked away, cut, or any combination thereof. The completed suturing is shown in FIG. 2F. Thus, the keratoprosthesis 56 is secured to the eye 36 temporarily during a secondary procedure as described herein.

The present teachings contemplate that the keratoprosthesis of FIG. 1A through FIG. 1C, or any other keratoprosthesis described herein may be employed in the method of FIG. 2A through FIG. 2F. The order of the method steps described herein may be performed in any order that is practicable.

Figures 3A, 3B:
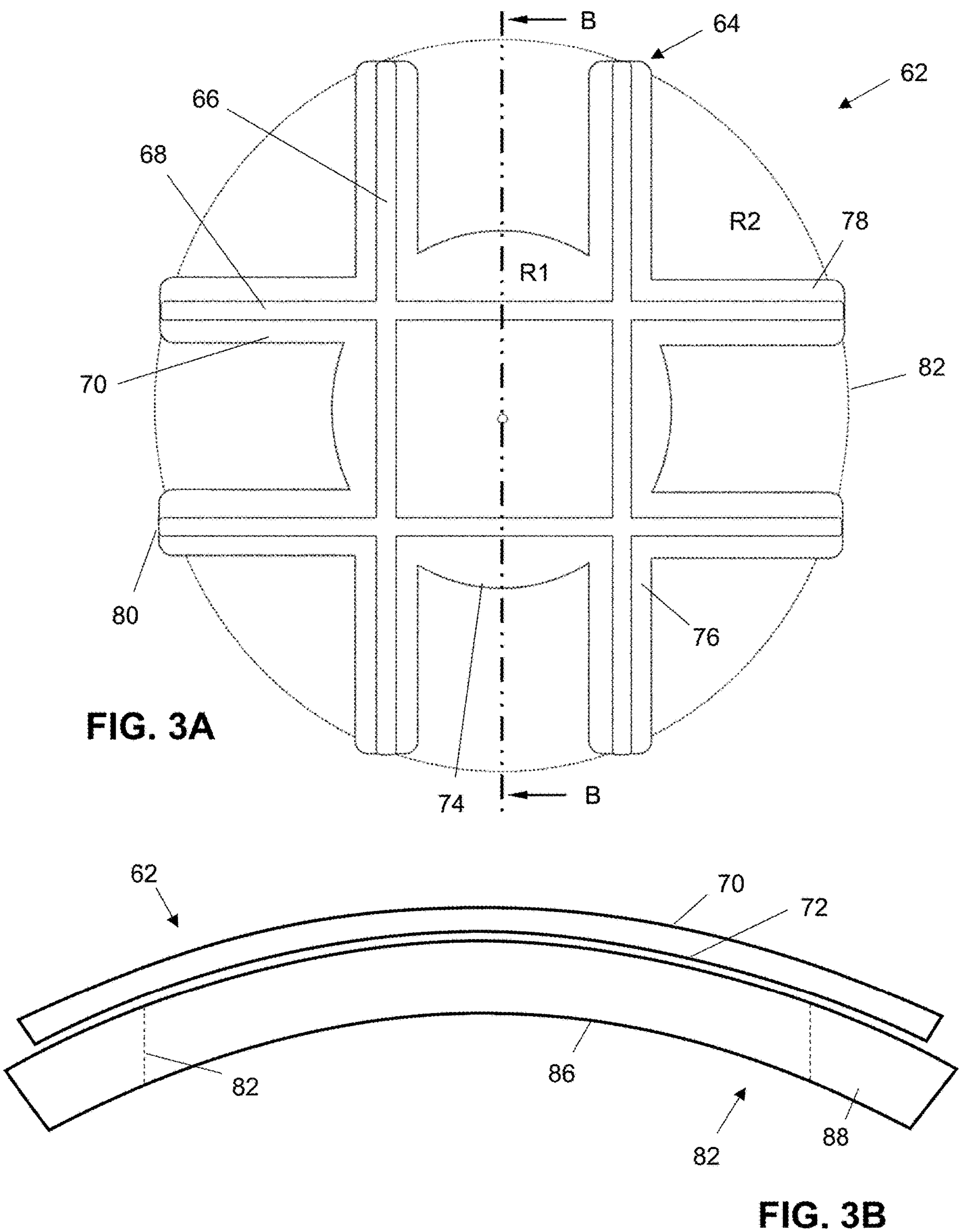
FIG. 3A is an anterior plan view of a suturing jig according to the present teachings.
FIG. 3B is a sectional view of the suturing jig viewed along a line B-B, on an eye.

FIG. 3A illustrates a corneal transplant suturing jig 62 according to the present teachings, which can function as a temporary exoskeleton overlying a corneal button. The corneal transplant suturing jig 62 comprises a body member 64 into which two first grooves 66 and two second grooves 68 are formed on a first side 70 thereof. The first side 70 opposes a second side 72 (shown in FIG. 3B) that is adapted to contact an eye. The first side 70 may be also referred to herein as the anterior side and the second side 72 may also be referred to herein as the posterior side.

The body member 64 comprises a central portion 74, two first projecting portions 76 extending generally in a first direction and two second projecting portions 78 extending generally in a second direction. The first grooves 66 extend along the entire length of the first projecting portions 76 and the second grooves 68 extend along the entire length of the second projecting portions 78. The grooves 66, 68 terminate at notches 80 formed on the perimeter of the body member 64.

The central portion 74 has a circular profile defined by a radius R1. The corneal transplant suturing jig 62 is adapted to be placed within an area of an incision 82 in the eye, the incision 82 having a circular profile defined by a radius R2.

FIG. 3B shows the corneal transplant suturing jig 62 of FIG. 3A located on a cornea 84 of the eye. The corneal transplant suturing jig 62 is defined by a radius of curvature RC3 that is generally equal to the radius of curvature RC4 of the cornea 84. The cornea 84 is shown with a first portion 86 and a second portion 88, and a demarcation line depicting where the incision 82 is made in the cornea 84. In a full thickness corneal transplant, the first portion 86 of the cornea 84 is removed and replaced with a button of a donor cornea. As shown in FIG. 3A, the notches 80 locate proximate to the perimeter of the incision 82 (e.g., on or within 1 mm of the perimeter) so sutures penetrate the second portion 88 of the cornea 84 and are located within the grooves 66, 68 to extend over the button of the donor cornea and hold the same in place.

The present teachings provide for a method of using the corneal transplant suturing jig 62 described above. The present teachings contemplate that the corneal transplant suturing jig of FIG. 3A and FIG. 3B, or any other corneal transplant suturing jig described herein may be employed with the method of or a similar method to FIG. 2A through FIG. 2F. The order of the method steps described herein may be performed in any order that is practicable.

In one aspect, the corneal transplant suturing jig 62 may be employed after removal of a temporary keratoprosthesis 56 from the eye, after the step shown in FIG. 2F and after completion of a retinal repair. In this regard, the same sutures as placed in FIG. 2A through FIG. 2D may be used to secure the corneal transplant suturing jig 62. After the step shown in FIG. 2F and after completion of a retinal repair, the first and second sutures 42, 48 may be untied and/or loosened, the temporary keratoprosthesis 56 may be removed, and the donor cornea button may be immediately located into the eye. Then, the corneal transplant suturing jig 62 may be located onto the eye and the first and second sutures 42, 48 may be tightened onto the corneal transplant suturing jig 62.

The present teachings contemplate that in some circumstances, a surgeon may not use the prior-placed first and second sutures 42, 48 to secure the corneal transplant suturing jig 62. There may be circumstances in which a surgeon decides to remove the first and second sutures 42, 48 and add new sutures to secure the corneal transplant suturing jig 62. In this regard, the first and second sutures 42, 48 may be removed and the steps shown in FIG. 2A through FIG. 2F may be repeated (whereby instead of the temporary keratoprosthesis 56, the corneal transplant suturing jig 62 is located onto the eye as in FIG. 2E and thereon the sutures are tightened as in FIG. 2F).

If new sutures are placed, the same marks and needle puncture holes created for the temporary keratoprosthesis 56 may be used or new marks and needle puncture holes may be created. The pattern of the new marks and needle puncture holes may be rotated at any angle (e.g., about 10° or more, 20° or more, 30° or more, or even 40° or more; about 80° or less, 70° or less, 60° or less, or even 50° or less) relative to the existing marks and needle puncture holes.

In another practicable method, two sets of sutures may be placed along the same paths at the outset of the surgery, one set to be used to secure the keratoprosthesis and the other suture set but left with slack, to be used later to affix the corneal transplant suturing jig after the first set has been removed.

In another aspect, the corneal transplant suturing jig 62 may be employed in a procedure where no temporary keratoprosthesis is used (e.g., a corneal transplant that is not performed in cooperation with a retinal repair). In this regard, the same method as depicted in FIG. 2A through FIG. 2F may be employed to make the marks 38, 40, locate the sutures 42, 48 relative to the marks 38, 40, form loops 44, 50, locating the corneal transplant suturing jig 62, and tightening the loops 44, 50. Instead of the keratoprosthesis 56 shown in FIG. 2E and FIG. 2F, the corneal transplant suturing jig 62, such as shown in FIG. 3A and FIG. 3B is located relative to the sutures 41, 28.

The sutures are gently snugged to keep the corneal transplant suturing jig and the donor cornea in a central position. Interrupted suture bites can then be taken from the donor cornea to the recipient host peripheral cornea in the spaces provided between the extending arms of the corneal transplant suturing jig. Once four or more interrupted sutures have been placed, the two original loop sutures set within the grooves of the jig can be lysed and removed. The remaining sutures securing the donor cornea more firmly to the host peripheral cornea can be placed according to surgeon preference. This process can be executed with or without an infusion cannula providing some degree of pressurization of the globe.

Figure 4A:
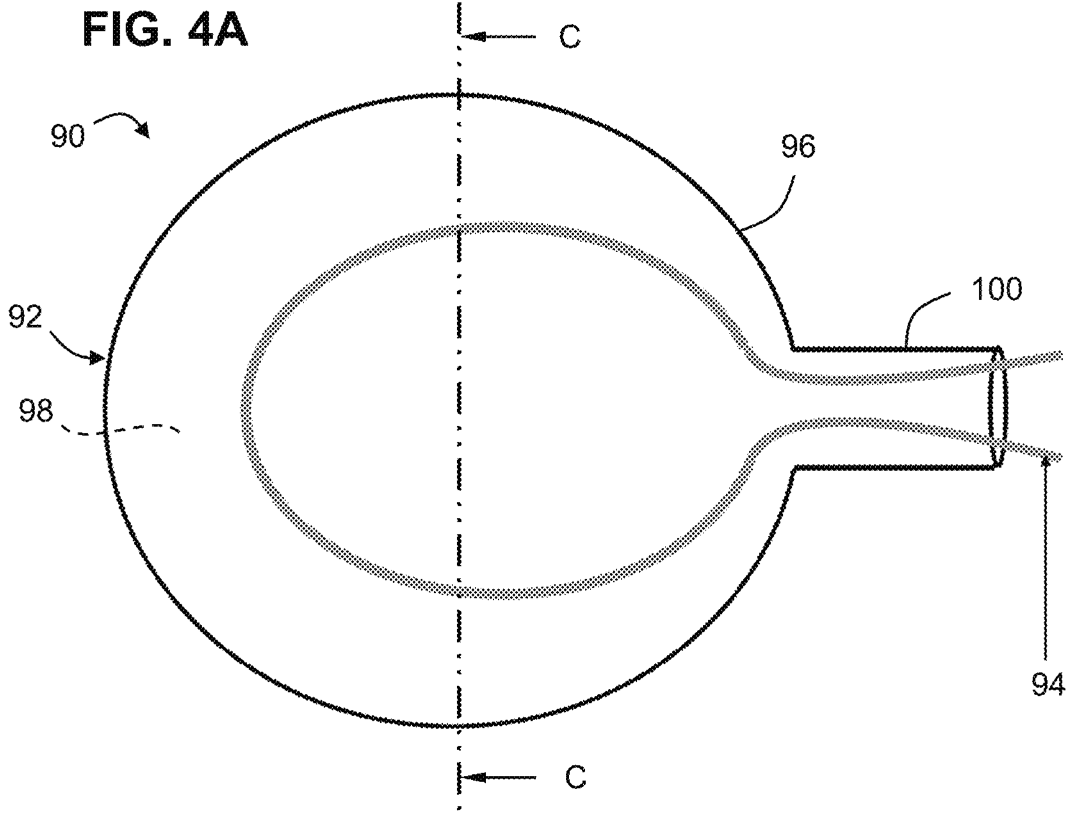
FIG. 4A is a plan view of a temporary endoprosthesis according to the present teachings.
Figure 4B:
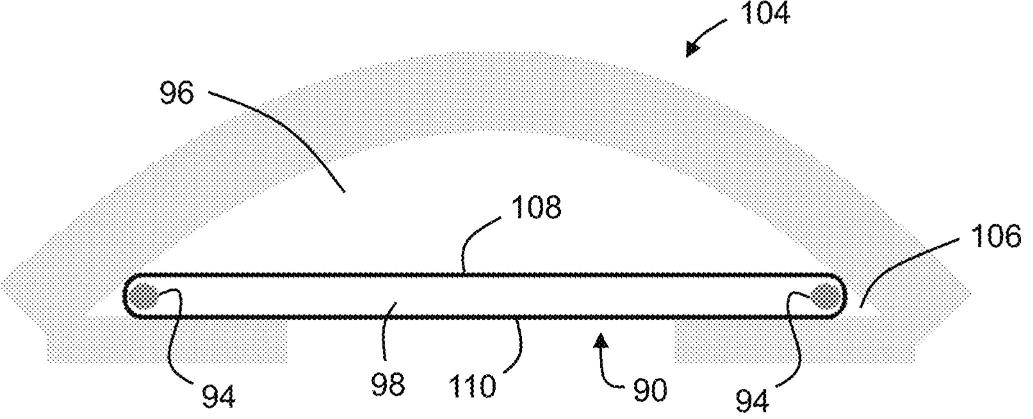
FIG. 4B is a sectional view of a temporary endoprosthesis according to the present teachings viewed along a line C-C.

In FIG. 4A and FIG. 4B, a temporary endoprosthesis 90 is shown. The temporary endoprosthesis 90 comprises a radially expansile diaphragm 92 and an obturator 94. By way of introducing the obturator 94 into the radially expansile diaphragm 92, which is flexible, radial expansion is realized.

The radially expansile diaphragm 92 includes a membrane 96 defining a cavity 98 and a neck 100, whereby the neck 100 provides access to the cavity 98. The neck 100 is configured to pass from an anterior chamber 102 of an eye 104, through an incision, and to an exterior of the eye 104.

As shown in FIG. 4B, an incision (e.g., a small peripheral limbal incision) may be formed in the eye 104 and the radially expansile diaphragm 92, in a flaccid form, may be fed through the incision and into the anterior chamber 96, leaving the neck 100 in and extending through the incision and exposed exterior to the eye 104.

While inside the anterior chamber 96, the obturator 94 is fed through the neck 100 and into the cavity 98. The obturator 94 may be flexible enough to feed or expand peripherally around the cavity 98 and rigid enough to maintain the radially expansile diaphragm 92 in an expanded state. An exemplary obturator 94 may include a nitinol wire confirming to ASTM F2063-18.

Drawing back to the portion of the procedure where the corneal button is removed (prior to placement of a donor cornea), the trephination diameter, or the intended trephination diameter of the corneal incision may be smaller than the diameter of the iridocorneal angle 106 and/or the radially expansile diaphragm 92 in the expanded state. The iridocorneal angle 106 of the eye 104 may be filled by the radially expansile diaphragm 92, in the expanded state, such that it separates the anterior chamber 96 from a posterior chamber (not shown) of the eye 104. Application of the obturator 94 effectively locks the radially expansile diaphragm 92 into the iridocorneal angle 106, creating an at least partially closed and pressurized system posterior to the diaphragm, even when the diseased host corneal button has been removed.

The temporary endoprosthesis 90 may find benefit being employed in cooperation with a temporary keratoprosthesis described herein. The temporary endoprosthesis 90 may eliminate or at least substantially mitigate depressurization during the open sky time, either during the initial trephination, or between removal of the temporary keratoprosthesis and securement of donor corneal button. Any air or oil tamponade placed during retinal detachment repair may be secured during placement of the donor corneal button.

After securement of the donor corneal button, the obturator 94 may be removed from the radially expansile diaphragm 92, which would return to its flaccid state. Thereafter, the radially expansile diaphragm 92 can be removed from the anterior chamber 102, through the incision 82.

FIG. 4B illustrates a cavity 98 continuous across a dimension (e.g., diameter) thereof. First and second segments 108, 110 of the membrane 96 define the cavity 98. In this regard, the obturator 94 may be elastically deformed (e.g., bent) and fed through the neck 100 and into the cavity 98. By elastic reformation, the obturator 94 may radially expand the diaphragm.

Figure 5B:
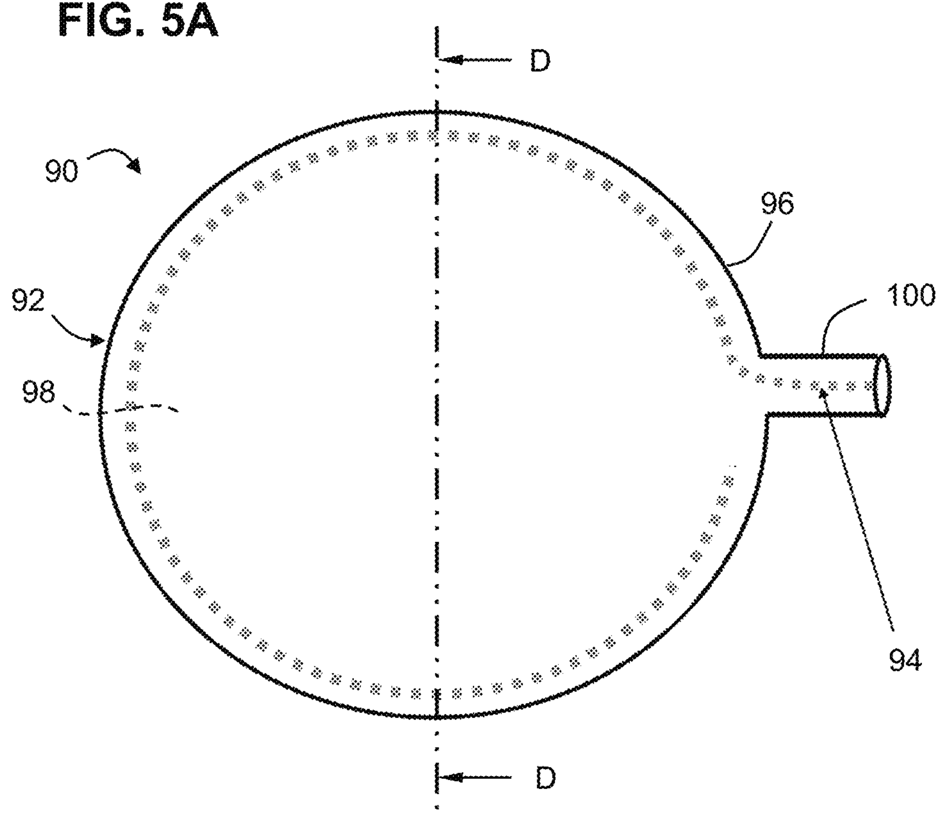
FIG. 5B is a sectional view of a temporary endoprosthesis according to the present teachings viewed along a line D-D.
Figure 5B:
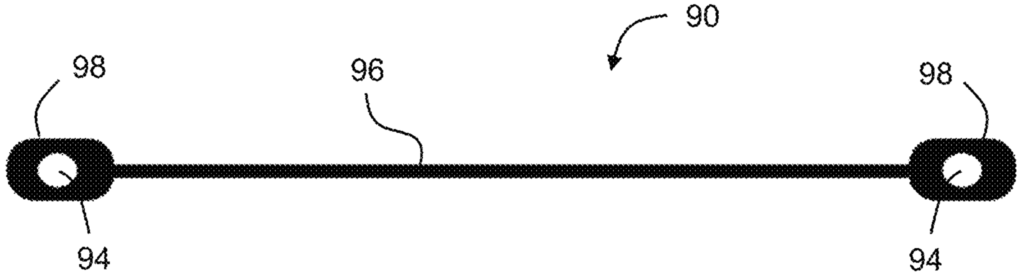

FIG. 5B illustrates a cavity 98 that is annular. In this regard, one end of the obturator 94 may be fed through the neck 100 and travel perimetrically through the cavity 98. The one end fed through the neck 100 may be fed. e.g., about 300° or more, 320° or more, 340° or more, or even 360° or more, around the cavity 98.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The terms "generally" or "substantially" to describe angular measurements may mean about +/−10° or less, about +/−5° or less, or even about +/−1° or less. The terms "generally" or "substantially" to describe angular measurements may mean about +/−0.01° or greater, about +/−0.1° or greater, or even about +/−0.5° or greater.

The terms "generally" or "substantially" to describe linear measurements may mean about +/−10% or less, about +/−5% or less, or even about +/−1% or less. The terms "generally" or "substantially" to describe linear measurements may mean about +/−0.01% or greater, about +/−0.1% or greater, or even about +/−0.5% or greater.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time, and the like is, for example, from 1 to 90, from 20 to 80, or from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints.

The term "consisting essentially of" to describe a combination shall include the elements, ingredients, components, or steps identified, and such other elements ingredients, components or steps that do not materially affect the basic and novel characteristics of the combination. The use of the terms "comprising" or "including" to describe combinations of elements, ingredients, components, or steps herein also contemplates embodiments that consist essentially of the elements, ingredients, components, or steps.

Plural elements, components, or steps can be provided by a single integrated element, component, or step. Alternatively, a single integrated element, component, or step might be divided into separate plural elements, components, or steps. The disclosure of "a" or "one" to describe an element, component, or step is not intended to foreclose additional elements, components, or steps.

REFERENCE NUMERALS

10 Keratoprosthesis
12 Body member

14 First side (anterior side) of the body member
16 Second side (posterior side) of the body member
18 Surface of the first side
20 First grooves
22 Second grooves
24 Notches
26 Radiused surface of the posterior side
28 Planar surface of the posterior side
30 Lip
32 Cornea
34 Limbus
36 Eye
38 Mark
40 Mark
42 First suture
44 Loop of the first suture
46 Free ends of the first suture
48 Second suture
50 Loop of the second suture
52 Free ends of the second suture
54 Trephination hole
56 Keratoprosthesis
58 Grooves
60 Notches
62 Corneal transplant suturing jig
64 Body member
66 First grooves
68 Second grooves
70 First side of the body member
72 Second side of the body member
74 Central portion of the body member
76 First projecting portions
78 Second projecting portions
80 Notches
82 Incision
84 Cornea
86 First portion of the cornea
88 Second portion of the cornea
90 Temporary endoprosthesis
92 Radially expansile diaphragm
94 Obturator
96 Membrane
98 Cavity
100 Neck
102 Anterior chamber
104 Eye
106 Iridocorneal angle
108 First segment
110 Second segment

What is claimed is:

1. A temporary keratoprosthesis for ophthalmological surgery comprising:

a body member having:

a perimeter, and a surface into which is defined a first groove extending generally in a first direction and/or a second groove extending generally in a second direction, the first and second grooves extending between two points arranged adjacent the perimeter of the body member, and the first and second grooves terminating at a notch arranged at each of the two points;

wherein the temporary keratoprosthesis has a configuration suitable for placement onto an eye and maintaining its general configuration during the ophthalmological surgery; and wherein the first and second grooves receive pre-placed sutures and prevent the sutures from migrating and/or obscuring a view through the body member.

2. The temporary keratoprosthesis according to claim 1, wherein the first and second grooves extend partially into a thickness of the body member; and wherein the first and second grooves have profiles, as viewed on transverse cross-sections of the first and second grooves, that is radiused and/or polygonal.

3. The temporary keratoprosthesis according to claim 2, wherein the first groove intersects the second groove; and optionally wherein the first and second directions are oriented about 90 degrees to each other.

4. The temporary keratoprosthesis according to claim 3, wherein the surface is on an anterior side of the temporary keratoprosthesis that is opposing a posterior side thereof, the posterior side being adapted to contact or at least orient toward the eye; and wherein the first and second grooves extend along an arc of the surface.

5. The temporary keratoprosthesis according to claim 4, wherein the temporary keratoprosthesis comprises two or more of the first groove and/or two or more of the second groove.

6. The temporary keratoprosthesis according to claim 5, wherein the two or more first grooves and the two or more second grooves define a boundary around a continuous portion of the surface;

wherein the boundary is adapted to generally align with and/or circumscribe an incision formed in the eye, as viewed along an axis extending through the temporary keratoprosthesis and an iris of the eye;

wherein the boundary is about 5 mm to 10 mm in its largest dimension, preferably about 8 mm; and wherein the boundary is adapted for light transmission through the anterior and posterior sides of the temporary keratoprosthesis and ultimately through the iris of the eye onto which the temporary keratoprosthesis is placed.

7. The temporary keratoprosthesis according to claim 6, wherein the two or more first grooves and the two or more second grooves form a grid on the surface, as viewed along an axis extending through the first and second sides of the body member; and wherein a center section of the grid generally aligns with and/or circumscribes the incision formed in the eye, as viewed along an axis extending through the temporary keratoprosthesis and an iris of the eye.

8. The temporary keratoprosthesis according to claim 7, wherein the first and second grooves are about 0.01 mm to 0.5 mm in their largest dimension as viewed on transverse cross-sections thereof, more preferably about 0.3 mm to 0.4 mm; and wherein a depth of the first and second grooves is generally equal to or less than a width of the first and second grooves, or vice versa.

9. The temporary keratoprosthesis according to claim 8, wherein two of the notches of the first and/or second grooves that are in immediate adjacent relationship to each other are separated by a distance of about 3 mm to 6 mm, preferably about 4.3 mm.

10. The temporary keratoprosthesis according to claim 9, wherein the body member is about 9 mm to 15 mm in a largest dimension of a profile thereof, preferably about 12 mm.

11. The temporary keratoprosthesis according to claim 10, wherein the body member is domed;

wherein the anterior side of the temporary keratoprosthesis has a radius of curvature of about 6.5 mm to 10 mm, preferably about 7 mm; and wherein the posterior side of the temporary keratoprosthesis has a radius of curvature of about 6.5 mm to 10 mm, preferably about 7 mm.

12. The temporary keratoprosthesis according to claim 11, wherein the posterior side of the temporary keratoprosthesis comprises a trunk projecting from a first surface of the posterior side and defining a second surface of the posterior side; and wherein a distance between the first and second surfaces is about 0.2 mm to 1.2 mm, preferably about 0.8 mm.

13. The temporary keratoprosthesis according to claim 12, wherein a minor thickness of the temporary keratoprosthesis is about 0.1 mm to 3 mm, preferably about 2 mm; and wherein a major thickness of the temporary keratoprosthesis is about 2 mm to 4.5 mm, preferably about 3.19 mm.

14. The temporary keratoprosthesis according to claim 13, wherein the trunk comprises a radiused surface that terminates at a lip;

wherein the lip is defined by a minor diameter of about 6 mm to 8.5 mm, preferably about 7.4 mm; and wherein the lip is defined by a major diameter of about 6.5 mm to 9 mm, preferably about 8 mm.

15. The temporary keratoprosthesis according to claim 14, wherein the temporary keratoprosthesis is fabricated from polymer, glass, or both; optionally wherein the polymer includes silicone, poly(methyl methacrylate), hydrophobic acrylic, hydrophilic acrylic, or any combination thereof; preferably the temporary keratoprosthesis is fabricated from poly(methyl methacrylate).

16. A method for using the temporary keratoprosthesis of claim 1 in a procedure for applying the temporary keratoprosthesis onto the eye of a patient in need of the temporary keratoprosthesis.

17. The method according to claim 16, wherein the method comprises making marks at locations where a suture needle is to penetrate the eye;

wherein the marks are made according to the temporary keratoprosthesis, a physical template, and/or a light guide; and wherein the temporary keratoprosthesis, the physical template, and/or the light guide are applied to the eye prior to making the marks;

wherein optionally the temporary keratoprosthesis, the physical template, and/or the light guide are removed from the eye after making the marks.

18. The method according to claim 17, wherein the method comprises:

pre-placing a first suture and a second suture in the eye according to the marks with the first and second sutures each forming a loop exterior of the eye and free ends of the first and second sutures are left accessible to the exterior of the eye, and optionally wherein the loop of the first suture is oriented 90° to the loop of the second suture;

making an incision in the eye, formed in the cornea, and detaching at least a portion of the cornea from the eye;

applying the temporary keratoprosthesis to the eye;

locating the loops of the first and second sutures within the first and second grooves of the temporary keratoprosthesis, respectively, and pulling the loops of the first and second sutures taught; and securing the free ends of the first and second sutures such that the free ends of the first and second sutures are located within the first and second grooves of the temporary keratoprosthesis, respectively; and optionally wherein the first and second sutures penetrate a limbus of the eye.

19. The method according to claim 18, wherein the method comprises:

removing the first and second sutures, or un-securing the free ends of the first and second sutures and providing slack to the loops of the first and second sutures;

removing the temporary keratoprosthesis from the eye; and locating a corneal button on the eye.

20. A kit comprising the temporary keratoprosthesis according to claim 1, the kit further comprising: a first suture, a second suture, a suture needle, a blade, a biocompatible ink, one or more medicaments, or any combination thereof.

* * * * *